(12) United States Patent
Cox et al.

(10) Patent No.: US 8,764,780 B2
(45) Date of Patent: Jul. 1, 2014

(54) APPARATUSES AND METHODS FOR FORMING INCISIONS IN OCULAR TISSUE

(75) Inventors: Mark A. Cox, Dallas, TX (US); Douglas C. Williamson, Coppell, TX (US); Andrew J. Scherer, Trabuco Canyon, CA (US); Timothy J. Payne, Santa Ana, CA (US); Rex O. Bare, Preston, CT (US)

(73) Assignee: Refocus Ocular, Inc., Dallas, TX (US)

( * ) Notice: Subject to any disclaimer, the term of this patent is extended or adjusted under 35 U.S.C. 154(b) by 0 days.

(21) Appl. No.: 13/313,789

(22) Filed: Dec. 7, 2011

(65) Prior Publication Data
US 2012/0078280 A1 Mar. 29, 2012

Related U.S. Application Data

(62) Division of application No. 12/260,694, filed on Oct. 29, 2008, now Pat. No. 8,083,759.

(60) Provisional application No. 61/001,593, filed on Nov. 2, 2007.

(51) Int. Cl.
A61F 9/00 (2006.01)

(52) U.S. Cl.
USPC .......................................... 606/166

(58) Field of Classification Search
USPC ................... 606/79, 107, 166, 167, 170, 176, 606/180–183; 30/286, 287, 388–390, 276; 70/20–25
See application file for complete search history.

(56) References Cited

U.S. PATENT DOCUMENTS

| | | | |
|---|---|---|---|
| 1,905,851 | A | 4/1933 | Green |
| 2,104,929 | A | 1/1938 | Kendall |
| 2,249,906 | A | 7/1941 | Longoria |
| 2,580,138 | A | 12/1951 | Trought |

(Continued)

FOREIGN PATENT DOCUMENTS

| | | |
|---|---|---|
| DE | 2226908 | 12/1972 |
| EP | 1 764 037 | 3/2007 |

(Continued)

OTHER PUBLICATIONS

Notification of Transmittal of the International Search Report and the Written Opnion of the International Searching Autority, or the Declaration dated Oct. 22, 2012 in connection with International Patent Application No. PCT/US12/49986.

(Continued)

*Primary Examiner* — Ryan Severson
*Assistant Examiner* — Katherine M Shi

(57) ABSTRACT

A surgical tool includes a surgical blade configured to be moved to form an incision. The surgical tool also includes a wire configured to cause movement of the surgical blade. The surgical tool further includes an actuator configured to shorten a length of the wire to cause the movement of the surgical blade. The surgical tool could be configured to move the surgical blade in a first direction and then in a second direction in response to a single shortening of the wire. Also, the wire could represent a first wire, the surgical tool could include a second wire, and the surgical tool could be configured to move the surgical blade in a first direction in response to shortening the first wire and to move the surgical blade in a second direction in response to shortening the second wire.

25 Claims, 23 Drawing Sheets

(56) References Cited

U.S. PATENT DOCUMENTS

| | | |
|---|---|---|
| 2,942,483 A | 6/1960 | Evans et al. |
| 3,814,213 A | 6/1974 | Balass |
| 5,314,441 A | 5/1994 | Cusack et al. |
| 5,441,510 A | 8/1995 | Simpson et al. |
| 5,618,294 A | 4/1997 | Aust et al. |
| 5,695,511 A | 12/1997 | Cano et al. |
| 6,077,287 A | 6/2000 | Taylor et al. |
| 6,080,172 A | 6/2000 | Fujiwara et al. |
| 6,409,740 B1 | 6/2002 | Kuhr et al. |
| 6,926,727 B2 | 8/2005 | Schachar et al. |
| 7,763,042 B2 | 7/2010 | Iio et al. |
| 7,901,421 B2 | 3/2011 | Shiuey et al. |
| 2002/0120284 A1 | 8/2002 | Schachar et al. |
| 2002/0120285 A1 | 8/2002 | Schachar et al. |
| 2003/0097080 A1 | 5/2003 | Esashi et al. |
| 2004/0199147 A1* | 10/2004 | Nishizawa et al. ............ 606/1 |
| 2006/0259060 A1 | 11/2006 | Whitson et al. |
| 2008/0234693 A1 | 9/2008 | Stefanchik |
| 2009/0157109 A1 | 6/2009 | Bare et al. |

FOREIGN PATENT DOCUMENTS

| | | |
|---|---|---|
| JP | 2003530975 A | 10/2003 |
| JP | 2004503276 A | 2/2004 |
| JP | 2005237964 A | 9/2005 |
| JP | 2007526084 A | 9/2007 |
| WO | WO 01/80935 A1 | 11/2001 |
| WO | WO 01/95783 | 12/2001 |
| WO | WO 03/013374 A1 | 2/2003 |
| WO | WO 2005/084557 | 9/2005 |

OTHER PUBLICATIONS

European Search Report dated Sep. 3, 2012 in connection with European Patent Application No. EP 12 17 7148.

International Search Report dated Apr. 14, 2009 in connection with International Patent Application No. PCT/US2008/081808.

Written Opinion of the International Searching Authority dated Apr. 14, 2009 in connection with International Patent Application No. PCT/US2008/081808.

Translation of Office Action dated Apr. 9, 2013 in connection with Japanese Patent Application No. 2011-258798.

Office Action dated May 14, 2013 in connection with U.S. Appl. No. 11/606,480.

Translation of Office Action dated Dec. 4, 2012 in connection with Japanese Patent Application No. 2010-532244.

Office Action dated Feb. 20, 2013 in connection with U.S. Appl. No. 13/205,359.

Extended European Search Report dated Oct. 16, 2013 in connection with European Application No. 13171854.6, 7 pages.

\* cited by examiner

APPARATUSES AND METHODS FOR FORMING INCISIONS IN OCULAR TISSUE

PRIORITY CLAIM

This application is a divisional of prior pending U.S. patent application Ser. No. 12/260,694 filed on Oct. 29, 2008.

This application claims priority under 35 U.S.C. §119(e) to U.S. Provisional Patent Application No. 61/001,593 filed on Nov. 2, 2007, which is hereby incorporated by reference.

CROSS-REFERENCE TO RELATED PATENT DOCUMENTS

This application is related to the following U.S. patent applications and issued patents:
(1) U.S. Pat. No. 6,007,578 entitled "Scleral Prosthesis for Treatment of Presbyopia and Other Eye Disorders" issued on Dec. 28, 1999;
(2) U.S. Pat. No. 6,280,468 entitled "Scleral Prosthesis for Treatment of Presbyopia and Other Eye Disorders" issued on Aug. 28, 2001;
(3) U.S. Pat. No. 6,299,640 entitled "Scleral Prosthesis for Treatment of Presbyopia and Other Eye Disorders" issued on Oct. 9, 2001;
(4) U.S. Pat. No. 5,354,331 entitled "Treatment of Presbyopia and Other Eye Disorders" issued on Oct. 11, 1994;
(5) U.S. Pat. No. 5,465,737 entitled "Treatment of Presbyopia and Other Eye Disorders" issued on Nov. 14, 1995;
(6) U.S. Pat. No. 5,489,299 entitled "Treatment of Presbyopia and Other Eye Disorders" issued on Feb. 6, 1996;
(7) U.S. Pat. No. 5,503,165 entitled "Treatment of Presbyopia and Other Eye Disorders" issued on Apr. 2, 1996;
(8) U.S. Pat. No. 5,529,076 entitled "Treatment of Presbyopia and Other Eye Disorders" issued on Jun. 25, 1996;
(9) U.S. Pat. No. 5,722,952 entitled "Treatment of Presbyopia and Other Eye Disorders" issued on Mar. 3, 1998;
(10) U.S. Pat. No. 6,197,056 entitled "Segmented Scleral Band for Treatment of Presbyopia and Other Eye Disorders" issued on Mar. 6, 2001;
(11) U.S. Pat. No. 6,579,316 entitled "Segmented Scleral Band for Treatment of Presbyopia and Other Eye Disorders" issued on Jun. 17, 2003;
(12) U.S. Pat. No. 6,926,727 entitled "Surgical Blade for Use with a Surgical Tool for Making Incisions for Scleral Eye Implants" issued on Aug. 9, 2005;
(13) U.S. Pat. No. 6,991,650 entitled "Scleral Expansion Device Having Duck Bill" issued on Jan. 31, 2006;
(14) U.S. patent application Ser. No. 10/080,877 entitled "System and Method for Making Incisions for Scleral Eye Implants" filed on Feb. 22, 2002;
(15) U.S. patent application Ser. No. 10/443,122 entitled "System and Method for Determining a Position for a Scleral Pocket for a Scleral Prosthesis" filed on May 20, 2003;
(16) U.S. patent application Ser. No. 11/137,085 entitled "Scleral Prosthesis for Treatment of Presbyopia and Other Eye Disorders" filed on May 24, 2005;
(17) U.S. patent application Ser. No. 11/199,591 entitled "Surgical Blade for Use with a Surgical Tool for Making Incisions for Scleral Eye implants" filed on Aug. 8, 2005;
(18) U.S. patent application Ser. No. 11/252,369 entitled "Scleral Expansion Device Having Duck Bill" filed on Oct. 17, 2005;
(19) U.S. patent application Ser. No. 11/323,283 entitled "Surgical Blade for Use with a Surgical Tool for Making Incisions for Scleral Eye Implants" filed on Dec. 30, 2005;
(20) U.S. patent application Ser. No. 11/323,284 entitled "System and Method for Making Incisions for Scleral Eye Implants" filed on Dec. 30, 2005;
(21) U.S. patent application Ser. No. 11/322,728 entitled "Segmented Scleral Band for Treatment of Presbyopia and Other Eye Disorders" filed on Dec. 30, 2005;
(22) U.S. patent application Ser. No. 11/323,752 entitled "Segmented Scleral Band for Treatment of Presbyopia and Other Eye Disorders" filed on Dec. 30, 2005;
(23) U.S. Provisional Patent Application No. 60/819,995 entitled "Apparatuses, Systems, and Methods Related to Treating Presbyopia and Other Eye Disorders" filed on Jul. 11, 2006;
(24) U.S. patent application Ser. No. 11/827,444 entitled "Apparatus and Method for Securing Ocular Tissue" filed on Jul. 11, 2007; and
(25) U.S. patent application Ser. No. 11/827,382 entitled "Scleral Prosthesis for Treating Presbyopia and Other Eye Disorders and Related Devices and Methods" filed on Jul. 11, 2007;
All of these U.S. patents and patent applications are hereby incorporated by reference.

TECHNICAL FIELD

This disclosure is generally directed to surgical devices and more specifically to apparatuses and methods for forming incisions in ocular tissue.

BACKGROUND

Various surgical procedures may be performed on a patient's eye to reduce or correct any number of vision problems. For example, surgical procedures are often performed to treat presbyopia, myopia, hyperopia, elevated intraocular pressure, ocular hypertension, and glaucoma. As a particular example, presbyopia can often be treated by implanting scleral prostheses within the scleral tissue of the patient's eye. For each individual scleral prosthesis, an incision can be made in the sclera of the eye. The incision can then be extended under the surface of the sclera to form a scleral "tunnel," and a scleral prosthesis can be placed within the tunnel. One or multiple scleral prostheses may be implanted in a patient's eye to partially or completely eliminate presbyopia in the patient's eye. The same or similar technique can also be used to treat glaucoma, ocular hypertension, elevated intraocular pressure, or other eye disorders. This technique is described more fully in the U.S. patents and patent applications incorporated by reference above.

SUMMARY

This disclosure provides apparatuses and methods for forming incisions in ocular tissue.

In a first embodiment, a surgical tool includes a surgical blade configured to be moved to form an incision. The surgical tool also includes a wire configured to cause movement of the surgical blade. The surgical tool further includes an actuator configured to shorten a length of the wire to cause the movement of the surgical blade.

In particular embodiments, the actuator is configured to shorten the length of the wire by applying an electrical current to the wire. The wire could, for example, include flexible nitinol.

In other particular embodiments, the surgical tool is configured to move the surgical blade in a first direction and then in a second direction in response to a single shortening of the wire.

In yet other particular embodiments, the wire represents a first wire, and the surgical tool also includes a plate coupled to a second wire that is configured to move the surgical blade. The surgical tool further includes a locomotive wheel configured to turn in response to the shortening of the first wire and a locomotive arm coupled to the locomotive wheel and the plate. Rotation of the locomotive wheel causes the locomotive arm to move the second wire.

In other particular embodiments, the wire represents a first wire, and the surgical tool also includes a second wire. The surgical tool is configured to move the surgical blade in a first direction in response to shortening the first wire and to move the surgical blade in a second direction in response to shortening the second wire.

In still other particular embodiments, the surgical tool further includes a third wire configured to move the surgical blade and first and second connectors. The first connector couples the first wire to the third wire such that the shortening of the first wire moves the surgical blade in the first direction. The second connector couples the second wire to the third wire such that the shortening of the second wire moves the surgical blade in the second direction.

In other particular embodiments, the surgical tool also includes a third wire configured to move the surgical blade. The surgical tool further includes a rocking arm coupled to the third wire and configured to rotate. In addition, the surgical tool includes first and second spring clips. The first spring clip is coupled to the first wire and the rocking arm such that the shortening of the first wire rotates the rocking arm clockwise. The second spring clip is coupled to the second wire and the rocking arm such that the shortening of the second wire rotates the rocking arm counter-clockwise.

In additional particular embodiments, the surgical tool also includes a third wire configured to move the surgical blade. The surgical tool further includes a rocking arm coupled to the first and third wires and configured to rotate such that the shortening of the first wire rotates the rocking arm clockwise. In addition, the surgical tool includes a spring clip coupled to the second wire and the rocking arm such that the shortening of the second wire rotates the rocking arm counter-clockwise.

In a second embodiment, a method includes shortening a length of a wire in a surgical tool by heating the wire. The method also includes moving a surgical blade based on the shortening of the wire.

In a third embodiment, a surgical tool includes a surgical blade configured to be moved to form an incision and a wire configured to cause movement of the surgical blade. The surgical tool also includes a central axle around which the wire is wrapped and first and second springs configured to rotate the central axle in first and second directions, respectively. The surgical tool further includes first and second latches configured to secure and release the first and second springs, respectively. The surgical tool also includes a switch assembly configured to cause the first latch to release the first spring so that the central axle rotates in the first direction, where the second latch is configured to release the second spring so that the central axle rotates in the second direction. In addition, the surgical tool includes a plunger configured to return at least one of the springs to a location for re-securing by at least one of the latches.

In particular embodiments, the surgical tool further includes first and second mechanical arms coupled to the plunger and configured to return the first and second springs to locations for re-securing by the first and second latches.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawing, in which.

DETAILED DESCRIPTION

Figure 1A:
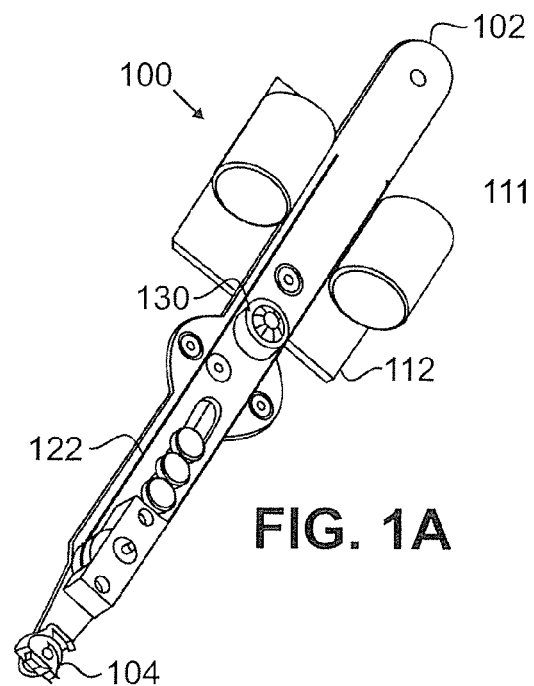
FIGS. 1A through 1D illustrate a first example surgical tool for making incisions in accordance with this disclosure.
Figure 1B:
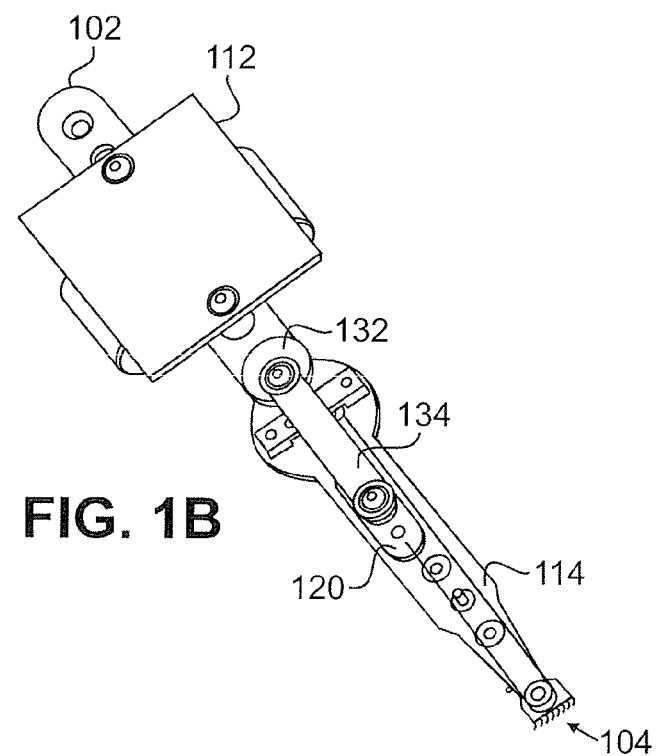
Figure 1C:
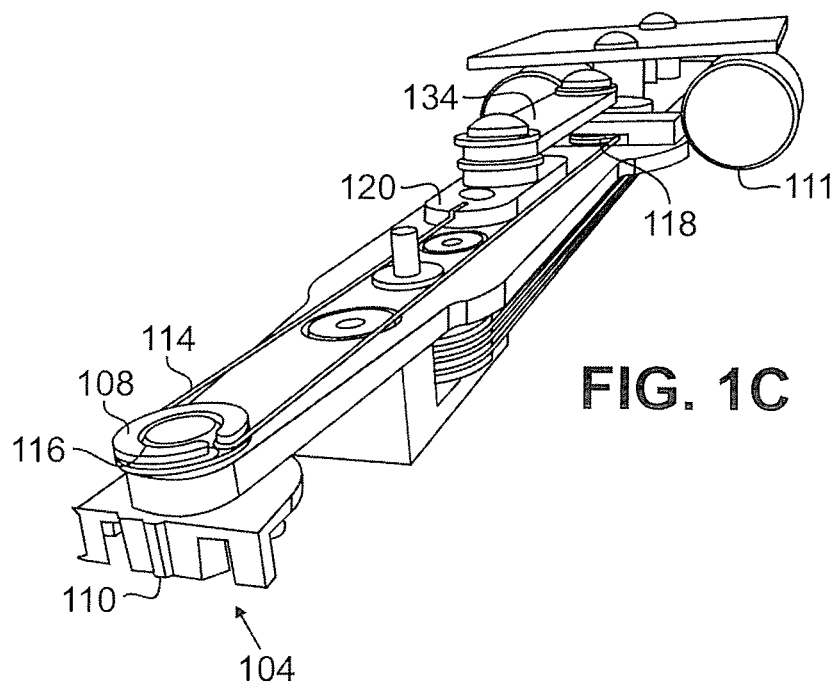
Figure 1D:
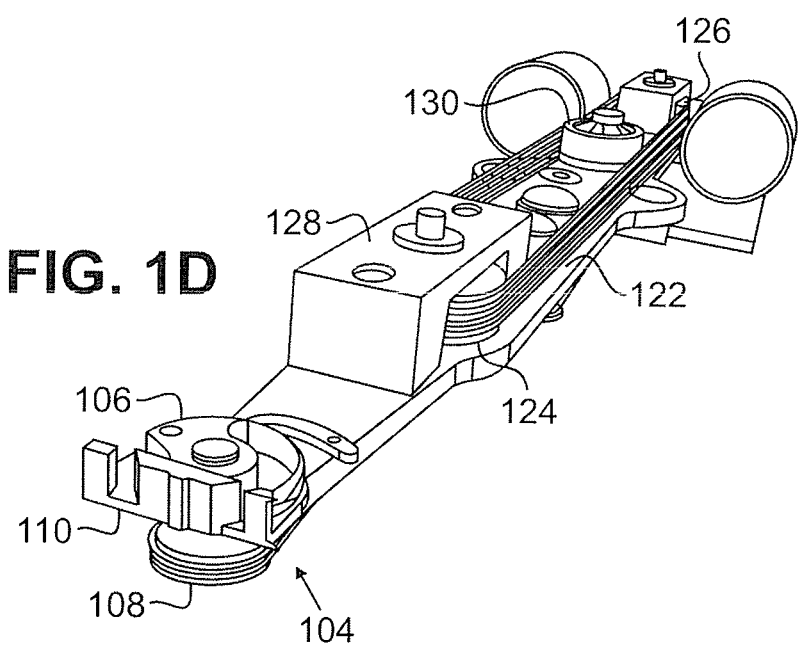

FIGS. 1A through 10B, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

FIGS. 1A through 1D illustrate a first example surgical tool 100 for making incisions in accordance with this disclosure. The embodiment of the surgical tool 100 shown in FIGS. 1A through 1D is for illustration only. Other embodiments of the surgical tool 100 could be used without departing from the scope of this disclosure.

As shown in FIGS. 1A through 1D, the surgical tool 100 includes a frame 102. The frame 102 represents a support structure on which other components of the surgical tool 100 can be mounted or secured. In this example, the frame 102 represents a generally straight and flat structure having various holes through which bolts, screws, pins, or other attachment mechanisms can be used to secure other various components of the surgical tool 100 to the frame 102. The frame 102 can be formed from any suitable material or materials, such as metal or plastic. The frame 102 can also have any suitable size, shape, and dimensions, which could vary depending on the layout and arrangement of the other components of the surgical tool 100.

In this example, the surgical tool 100 also includes a surgical blade assembly 104. The surgical blade assembly 104 includes a surgical blade 106, a rotating wheel 108, and a footplate 110. The surgical blade 106 is used to physically form an incision in the ocular tissue of a patient's eye. In this example, the surgical blade 106 includes a central portion and a curved cutting blade coupled to the central portion. The central portion of the surgical blade 106 can be rotated by the surgical tool 100. Rotation of the central portion of the surgical blade 106 therefore results in movement of the cutting blade. By rotating the central portion of the surgical blade 106 in one direction, the cutting blade can be moved into the ocular tissue of the patient's eye. By rotating the central portion of the surgical blade 106 in the opposite direction, the cutting blade can be retracted from the ocular tissue of the patient's eye. In this example, the surgical blade 106 includes a curved cutting blade that can be used (among other things) to form scleral tunnels in the scleral tissue of the patient's eye. However, the surgical blade 106 could be used to form any other suitable incision, and the surgical blade 106 could use any suitable type of cutting blade (curved or otherwise).

The central portion of the surgical blade 106 is coupled to the rotating wheel 108. Because of this, rotation of the rotating wheel 108 causes a corresponding rotation of the surgical blade 106. By controlling the rotation of the rotating wheel 108, the surgical tool 100 can control the rotation of the surgical blade 106 (and therefore the creation of an incision). In this example embodiment, as described in more detail below, the surgical tool 100 is configured to cause bi-directional rotation of the rotating wheel 108, thereby causing bi-directional rotation of the surgical blade 106 (into and then out of the patient's ocular tissue). The rotating wheel 108 includes any suitable structure facilitating rotation of and control over the surgical blade 106.

The footplate 110 represents a structure that can be placed onto the surface of the patient's eye. The footplate 110 allows the surgical tool 100 to be positioned properly on the patient's eye to ensure that any incisions made with the surgical tool 100 are in the proper positions on the patient's eye. As shown here, the footplate 110 includes two notches, which allow the curved cutting blade of the surgical blade 106 to pass through the footplate 110 and into and out of the patient's ocular tissue. The footplate 110 includes any suitable structure facilitating placement of the surgical tool 100 on the patient's eye.

The surgical tool 100 also includes one or more power supplies 111. The power supplies 111 provide operating power to the surgical tool 100, such as power used to cause rotation of the surgical blade 106. The power supplies 111 include any suitable source of power for the surgical tool 100, such as batteries, solar cells, fuel cells, or any other or additional power supply or supplies. As a particular example, the power supplies 111 could represent camera or camcorder batteries, such as 1.5V batteries. While the surgical tool 100 in this example includes two power supplies 111, any suitable number of power supplies 111 could be used in the surgical tool 100 (including a single power supply).

A printed circuit board 112 implements various logic for controlling the surgical tool 100. For example, the printed circuit board 112 could include control logic for controlling the rotation of the surgical blade 106. The printed circuit board 112 could also include communication circuitry for communicating with external components or systems. As a particular example, the printed circuit board 112 could include components facilitating wired or wireless communications, such as infrared or radio frequency (RF) communications. The wired or wireless communications could be used for any suitable purpose. For instance, the printed circuit board 112 could communicate with an audible, sensory (vibration), or visual mechanism (within or external to the surgical tool 100). The audible, sensory, or visual mechanism could inform a surgeon or other personnel of the status of the surgical tool 100. Example statuses could include: the tool is properly located and ready for use, the surgical blade is moving forward, the surgical blade is moving backward, the surgical blade's cycle has been interrupted, the surgical blade's cycle has been successfully completed, and potentially other miscellaneous information. The printed circuit board 112 could also receive signals (such as from a foot pedal, from a switch on the tool 100, or from a wired or wireless device) for initiating rotation of the surgical blade 106. Any other suitable wired or wireless communications may occur with the printed circuit board 112, and the printed circuit board 112 could support any other or additional functions.

In this example, the surgical tool 100 includes a wire 114, which is used to cause rotation of the rotating wheel 108 (thereby causing rotation of the surgical blade 106). The wire 114 could be formed from any suitable material or materials, such as Kevlar. The wire 114 could also have any suitable shape, such as a strand of material(s) having a circular or ovoidal cross section (although other shapes having over cross sections could be used).

The wire 114 is inserted into, coupled to, secured against, or otherwise associated with the rotating wheel 108. In this example, the wire 114 is inserted into a channel 116 in the rotating wheel 108. The channel 116 retains the wire 114, which allows movement of the wire 114 to translate into rotation of the rotating wheel 108. The wire 114 is also wrapped around a wheel 118. The wheel 118 rotates and allows back and forth movement of the wire 114. In addition, a plate 120 is secured or attached to the wire 114. As explained in more detail below, the plate 120 can be moved generally up and down along the frame 102, which imparts bi-directional rotation to the wire 114. The bi-directional rotation of the wire 114 results in bi-directional rotation of the rotating wheel 108, which causes bi-directional rotation of the surgical blade 106. The wheel 118 includes any suitable structure allowing bi-directional rotation of the wire 114. The plate 120 includes any suitable structure for causing movement of the wire 114.

Another wire 122 is used to initiate the bi-directional rotation of the wire 114. The wire 122 is electrically connected to the printed circuit board 112. The wire 122 is formed from a material or materials that allow the wire 122 to be shortened in length. For example, the wire 122 could be formed from flexinol or flexible nitinol (nickel titanium naval ordnance). Flexinol wires shorten in length in response to heating, and the printed circuit board 112 includes any suitable structure(s) for heating the wire 122, such as by applying an electrical current to the wire 122. As a particular example, the printed circuit board 112 could apply an electrical current to the wire 122 to heat the wire 122 to at least approximately 100° C. This heating causes the wire 122 to shorten in length. As described in more detail below, this shortening of the wire 122 causes movement of the plate 120, which leads to rotation of the surgical blade 106. The wire 122 could be formed from any suitable material or materials, such as flexinol. The wire 122 could also have any suitable shape, such as a strand of material(s) having a circular or ovoidal cross section (although other shapes having over cross sections could be used).

In this example, the wire 122 is wrapped around two sets of pulleys 124-126. These sets of pulleys 124-126 allow the wire 122 to have a relatively long length while reducing the amount of space needed for the wire 122. In this particular embodiment, each set of pulleys 124-126 includes four pulleys that are independent of one another. Moreover, a support cover 128 is secured over each set of pulleys 124-126, which allows a central axle to be inserted through and allow rotation of each set of pulleys 124-126.

The wire 122 is also wrapped around or coupled to a central wheel 130. The central wheel 130 is attached or secured to a locomotive wheel 132 on the opposite side of the frame 102. A locomotive arm 134 is rotatably attached to the locomotive wheel 132 and the plate 120. When the wire 122 is shortened in length (such as by applying an electrical current to the wire 122), the shortening of the wire 122 causes rotation of the central wheel 130. Since the central wheel 130 is coupled to the locomotive wheel 132, the rotation of the central wheel 130 causes a corresponding rotation of the locomotive wheel 132.

Rotation of the locomotive wheel 132 causes the locomotive arm 134 to generally move up and down the frame 102, which also causes the plate 120 to generally move up and down the frame 102. As noted above, movement of the plate 120 up and down the frame 102 results in rotation of the wire 114 in one direction and then in the other direction. The use of the locomotive wheel 132 allows single-directional rotation of the central wheel 130/locomotive wheel 132 to translate into bi-directional rotation of the wire 114 (and therefore bi-directional rotation of the surgical blade 106). For instance, the wire 122 could shorten by an amount that causes approximately 360° of rotation of the central wheel 130/locomotive wheel 132, which results in an approximately 180° rotation of the surgical blade 106 into the patient's ocular tissue followed by an approximately 180° rotation of the surgical blade 106 out of the patient's ocular tissue. As a result, the surgical blade 106 can be rotated into and then out of the ocular tissue of the patient's eye to create an incision during a single application of electrical current to the wire 122.

In particular embodiments, the central wheel 130 can only rotate in a single direction. For example, the central wheel 130 could include a one-way clutch, such as a clutch formed from ball bearings that permit rotation in one direction but lock up and prevent rotation in the opposite direction. In these embodiments, the one-way central wheel 130 may allow rotation of the locomotive wheel 132 when the wire 122 is shortened using an electrical current, while preventing opposite rotation of the locomotive wheel 132 later (such as after the electrical current has stopped and the wire 122 has cooled).

After an incision has been made, the surgical tool 100 can be removed from the patient's eye. During this time, the wire 122 may cool due to the lack of an electrical current. In some embodiments, at this point, the wire 122 can be stretched to regain a longer length and approximate its precharged condition, so that the surgical tool 100 can be reused to form another incision in the patient's eye. The wire 122 can be stretched to regain a longer length in any suitable manner. For example, the wire 122 could be manually pulled in one or more locations to increase the length of the wire 122. As another example, the wire 122 could be detached from the central wheel 130 and pulled to increase its length. Further, a spring-loaded mechanism or other suitable mechanical mechanism could be incorporated into the surgical tool 100 to pull on the wire 122 when activated by a user. Any other suitable mechanical, electrical, or other mechanism(s) could be used to lengthen the wire 122 after use, preparing for the next incision cycle.

The surgical tool 100 could include any other or additional components according to particular needs. For example, any suitable type of connector or connectors (such as bolts, screws, pins, or other attachment mechanisms) can be used to couple various components of the surgical tool 100 to the frame 102 or to one another. Also, spacers or other suitable separating mechanisms could be used to separate various components from one another, such as to separate the printed circuit board 112 from the frame 102.

Figure 2A:
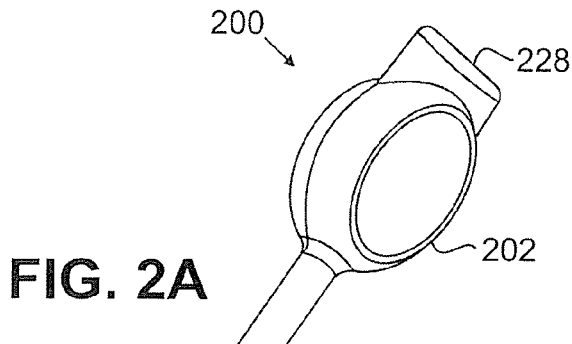
FIGS. 2A through 2C illustrate a second example surgical tool for making incisions in accordance with this disclosure.
Figure 2B:
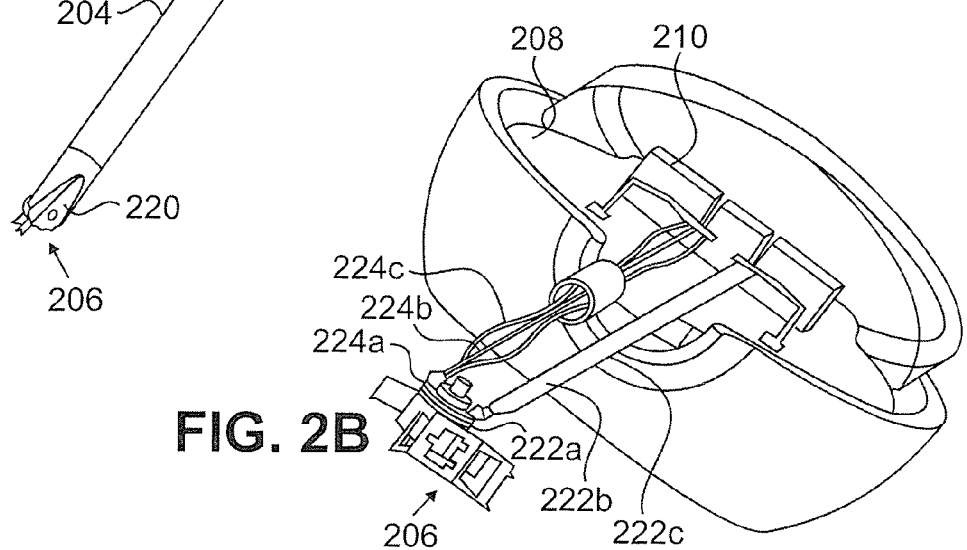
Figure 2C:
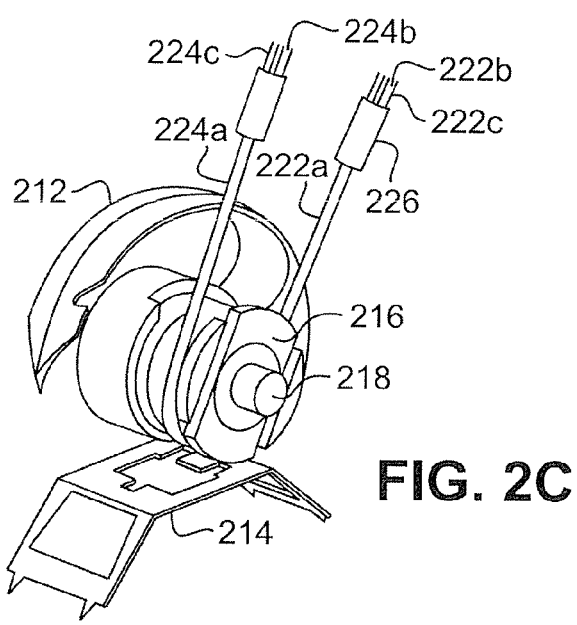

FIGS. 2A through 2C illustrate a second example surgical tool 200 for making incisions in accordance with this disclosure. The embodiment of the surgical tool 200 shown in FIGS. 2A through 2C is for illustration only. Other embodiments of the surgical tool 200 could be used without departing from the scope of this disclosure.

In this example, the surgical tool 200 includes a body 202, a shaft 204, and a surgical blade assembly 206 at a tip of the shaft 204. The body 202 in this embodiment may include various components used to operate and control the surgical tool 200. For example, the body 202 could retain or include a printed circuit board 208. The printed circuit board 208 could support various functions performed by the surgical tool 200, such as by enabling rotation of a surgical blade. In this example embodiment, the printed circuit board 208 includes connection blocks 210, which are used to hold or retain various wires in the surgical tool 200.

The surgical blade assembly 206 in this example includes a surgical blade 212 and a footplate 214. In FIGS. 2B and 2C, the shaft 204 of the surgical tool 200 has been removed for ease of explanation. As shown here, the surgical blade 212 includes a central portion 216 with a projection 218. The central portion 216 projects out from the actual cutting blade of the surgical blade 212, and the projection 218 projects farther out from the central portion 216. Each side of the surgical blade 212 could include a projection 218, and the projections 218 could be inserted into corresponding holes 220 near the tip of the shaft 204. In this way, the surgical blade 212 can be inserted into and retained within the shaft 204 of the surgical tool 200. This also allows rotation of the surgical blade 212 once inserted into the shaft 204 of the surgical tool 200.

The footplate 214 is mounted at or near the end of the shaft 204 and can be placed on the patient's eye. The footplate 214 in this example includes two notches through which the curved cutting blade of the surgical blade 212 can pass when making an incision. The footplate 214 also includes prongs for digging into the ocular tissue of the patient's eye to secure the footplate 214 in place. The footplate 214 in this example could be mounted so that the footplate 214 can rock back and forth on the end of the surgical tool 200.

As shown in FIGS. 2B and 2C, the surgical tool 200 includes two sets of wires 222a-222c and 224a-224c. Each set of wires in this example includes three wires. One wire 222a and 224a in each set may be formed from Kevlar or other material(s) and are wrapped around the central portion 216 of the surgical blade 212. Here, the wires 222a and 224a are wrapped around the central portion 216 in opposite directions. Another wire 222b and 224b in each set may be formed from flexinol or other material(s) that can be shortened in length. The third wire 222c and 224c in each set may represent ground wires.

As shown here, each set of wires includes a connector 226. The connector 226 in each set physically couples the wires in that set together. The connector 226 in each set of wires may also electrically couple the wires 222b and 222c or the wires 224b and 224c (thereby coupling each flexinol or other wire to ground). Each of the wires may represent any suitable strand of material(s) having any suitable size, shape, and cross section. Each of the connectors 226 includes any suitable structure for coupling multiple wires together.

In this example, the surgical tool 200 uses multiple wires to cause bi-directional rotation of the surgical blade 212. For example, an electrical current can be applied to the wire 222b, causing that wire to contract or shorten. Because of the connector 226 in that set of wires 222a-222c, this pulls on the wire 222a in that set of wires. Because the wire 222a in that set of wires is wrapped around the central portion 216 of the surgical bade 212, this pulls the surgical blade 212 in one direction, rotating the cutting blade into the ocular tissue of the patient's eye.

The electrical current through the wire 222b in the set of wires can stop, allowing that wire to cool. At the same time or after that, an electrical current can be applied to the wire 224*b* in the other set of wires 224*a*-224*c*. This causes the wire 224*b* in that set of wires to contract or shorten. Again, because of the connector 226 connecting that second set of wires 224*a*-224*c*, this pulls on the wire 224*a* in that set of wires, which is wrapped around the central portion 216 of the surgical bade 212 (but in the opposite direction). This pulls the surgical blade 212 in the opposite direction, rotating the cutting blade out of the ocular tissue of the patient's eye. This completes the formation of the incision. The electrical current through the red wire in the second set of wires 224 can stop, allowing that wire to cool.

In this type of surgical tool 200, multiple wires that can shorten in length (wires 222*b* and 224*b*) are used to rotate the surgical blade 212 in opposite directions. As a result, it may not be necessary to use any type of mechanism for stretching the contracting wires 222*b* and 224*b* in the surgical tool 200. For example, the pulling caused by shortening one wire 222*b* can pull the other wire 224*b*, lengthening the other wire 224*b*. However, the use of manual or automatic stretching of the wires 222*b* and 224*b* to a longer length, approximating its precharged condition, could be used in the surgical tool 200.

As with the surgical tool 100, the surgical tool 200 could be controlled in any suitable manner. For example, the printed circuit board 208 could include a wired or wireless interface for receiving commands and transmitting status information. The surgical tool 200 could also include a manual switch that can be used to control the surgical tool 200. For instance, a switch 228 at the top of the surgical tool 200 could be used to control the surgical tool 200. In some embodiments, depressing the switch 228 could initiate rotation of the surgical blade 212 in one direction, and release of the switch 228 could initiate rotation of the surgical blade 212 in the other direction. In other embodiments, depressing and releasing the switch 228 could initiate rotation of the surgical blade 212 in one direction, and depressing and releasing the switch 228 could initiate rotation of the surgical blade 212 in the other direction. However, this represents merely two examples of how the operation of the surgical tool 200 could be controlled. The surgical tool 200 could be controlled in any other suitable manner.

Figure 3A:
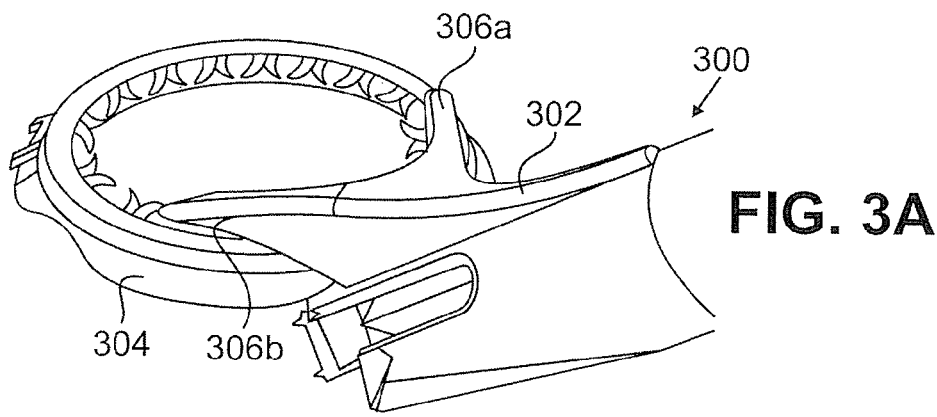
FIGS. 3A through 3C illustrate a third example surgical tool for making incisions in accordance with this disclosure.
Figure 3B:
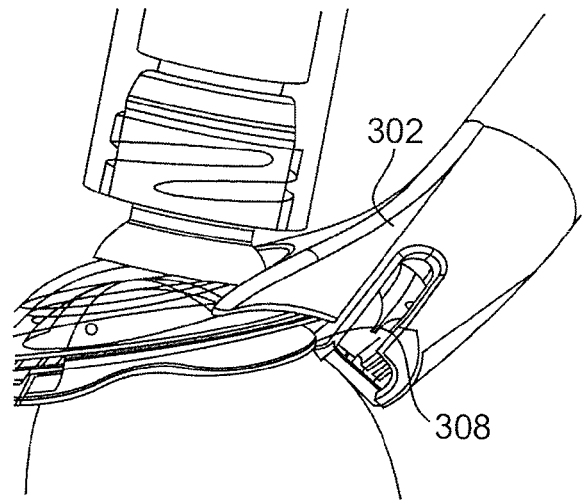
Figure 3C:
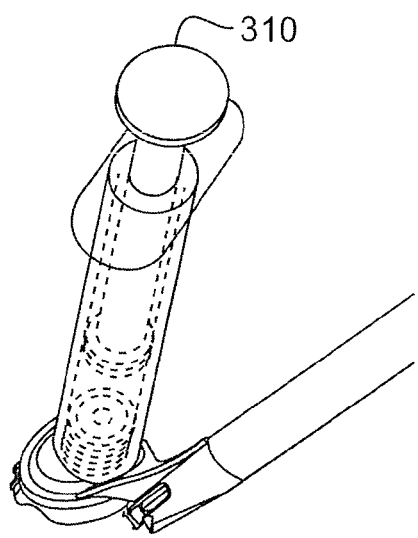

FIGS. 3A through 3C illustrate a third example surgical tool 300 for making incisions in accordance with this disclosure. The embodiment of the surgical tool 300 shown in FIGS. 3A through 3C is for illustration only. Other embodiments of the surgical tool 300 could be used without departing from the scope of this disclosure.

In this example, the surgical tool 300 could represent or operate in the same or similar manner as any of the surgical tools described in this patent document. The surgical tool 300 could, for example, include one or more wires formed from flexinol or other material(s) that can contract or shorten, such as in response to an electrical current. These one or more wires can be used to impart rotation to a surgical blade in the surgical tool 300 to form an incision in the ocular tissue of a patient's eye.

In addition, the surgical tool 300 in this example includes a mounting projection 302, which can be used to mount the surgical tool 300 on an ocular fixation device 304. The ocular fixation device 304 represents a device that is attached or secured to the patient's eye, thereby helping to reduce or prevent movement of the patient's eye during a surgical procedure. Various examples of ocular fixation devices are provided in U.S. patent application Ser. No. 11/827,444, which has been incorporated by reference. While one specific ocular fixation device 304 is shown here, any other suitable ocular fixation device 304 could be used with the surgical tool 300.

As shown here, the mounting projection 302 on the surgical tool 300 includes two extensions 306*a*-306*b* forming a partial circle around a dome of the ocular fixation device 304. Each of the extensions 306*a*-306*b* includes an end that can be inserted into a hole in the dome of the ocular fixation device 304. As shown in FIG. 3B, the mounting projection 302 of the surgical tool 300 also includes a stopper 308, which can be depressed against the ocular fixation device 304. Collectively, the ends of the extensions 306*a*-306*b* and the stopper 308 represent three points that can be used to mount the surgical tool 300 on the ocular fixation device 304 in one or more specific locations to ensure the proper positioning of the surgical tool 300 on the patient's eye. However, the use of the extensions 306*a*-306*b* and the stopper 308 to mount the surgical tool 300 on the ocular fixation device 304 is for illustration only. Any other suitable technique, structure, or mechanism could be used to mount, couple, attach, or otherwise associate the surgical tool 300 and the ocular fixation device 304.

In this example embodiment, the extensions 306*a*-306*b* of the surgical tool 300 form a partial circle around the dome of the ocular fixation device 304. This allows the surgical tool 300 to be attached or mounted to the ocular fixation device 304 while leaving a large portion of the ocular fixation device 304 exposed. Among other things, this may allow the use of a positioning tool 310, which can be used to place the ocular fixation device 304 into one or more positions on the patient's eye. In this example, the positioning tool 310 represents a spring-loaded syringe, which attaches to the ocular fixation device 300 by creating a vacuum against the dome, although any other suitable positioning tool could be used.

FIGS. 4A through 4I illustrate a fourth example surgical tool 400 for making incisions in accordance with this disclosure. The embodiment of the surgical tool 400 shown in FIGS. 4A through 4I is for illustration only. Other embodiments of the surgical tool 400 could be used without departing from the scope of this disclosure.

Figure 4A:
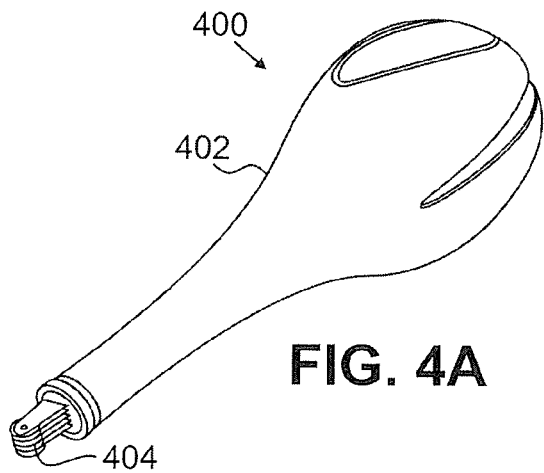
FIGS. 4A through 4I illustrate a fourth example surgical tool for making incisions in accordance with this disclosure.
Figure 4B:
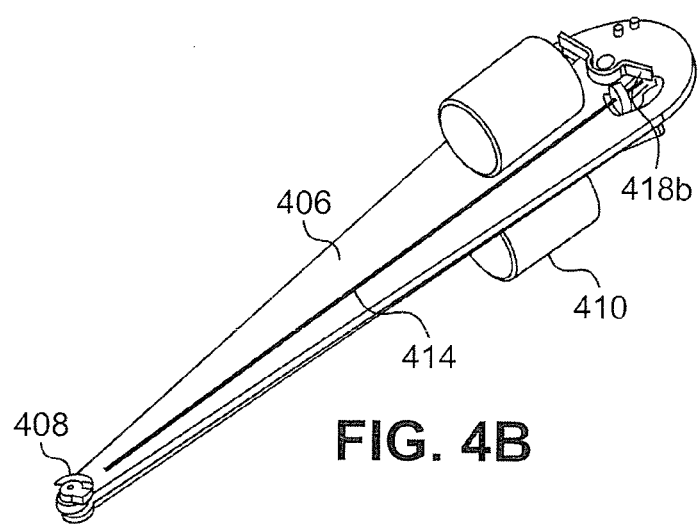
Figure 4C:
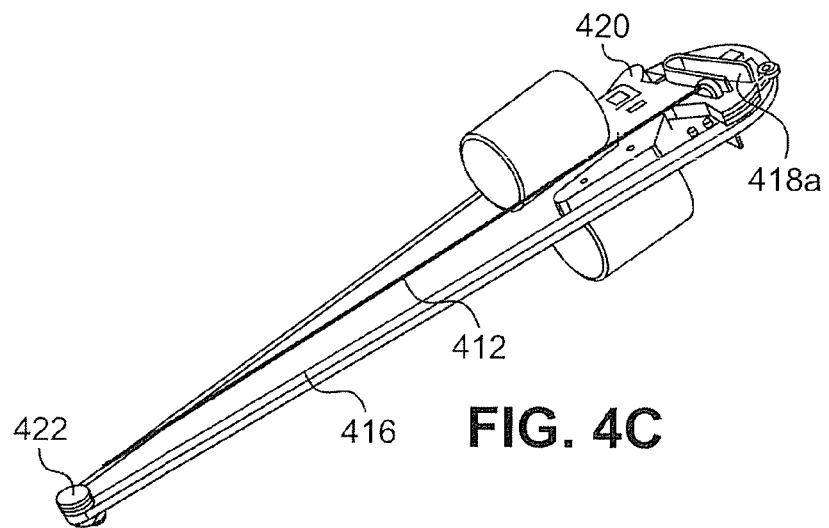

As shown in FIG. 4A, the surgical tool 400 includes a housing 402 and a blade assembly 404. The housing 402 generally contains the various components of the surgical tool 400 for causing rotation of a surgical blade in the blade assembly 404. Components within the housing 402 are shown in FIGS. 4B and 4C. For example, a printed circuit board 406 could support various functions performed by the surgical tool 400, such as by enabling and controlling rotation of a surgical blade 408. Also, one or more power supplies 410, such as one or more batteries, can supply power to the surgical tool 400.

In this example, the surgical tool 400 creates bi-directional rotation in the surgical blade 408 using three wires 412-416. One wire 412 extends generally from a position near the blade assembly 404 to a spring clip 418*a*, and another wire 414 extends generally from a position near the blade assembly 404 to a spring clip 418*b* (on the opposite side of the printed circuit board 406). The third wire 416 forms a loop between an upper rocking arm 420 and a lower pulley 422. Each of the wires 412-416 could be formed from any suitable material(s). For instance, the wires 412-414 could be formed from flexinol or other material(s) that can contract, and the wire 416 could be formed from Kevlar. Each of the wires 412-416 could also have any suitable shape, such as a strand of material(s) having a circular or ovoidal cross section (although other shapes having over cross sections could be used).

In this example embodiment, the spring clip 418*a* and the spring clip 418*b* facilitate bi-directional movement of the rocking arm 420 (and therefore bi-directional rotation of the wire 416) by providing tension on the drive wires 412-414.

The wire 412 is arranged to pull on the spring clip 418a to cause movement of the rocking arm 420 in one direction, and the wire 414 is arranged to pull on the spring clip 418b to cause movement of the rocking arm 420 in the opposite direction. Because of this, the wire 412 can impart directional rotation in one direction to the wire 416 (via the spring clip 418a and the rocking arm 420), and the wire 414 can impart directional rotation in the opposite direction to the wire 416 (via the spring clip 418b and the rocking arm 420).

The wire 416 is looped around the rocking arm 420 and the pulley 422, and the pulley 422 is coupled or secured to the surgical blade 408. Rotation of the wire 416 can therefore cause a corresponding rotation in the surgical blade 408. The printed circuit board 406 in this example could contain structures for causing contraction of the wires 412-414, such as by heating the wires 412-414 through application of electrical current to the wires 412-414. The printed circuit board 406 may therefore heat the wires 412-414 to impart bi-directional movement to the rocking arm 420. For example, applying an electrical current to the wire 412 could cause the surgical blade 408 to rotate into the patient's ocular tissue, and applying an electrical current to the wire 414 could cause the surgical blade 408 to rotate out of the patient's ocular tissue.

Figure 4D:
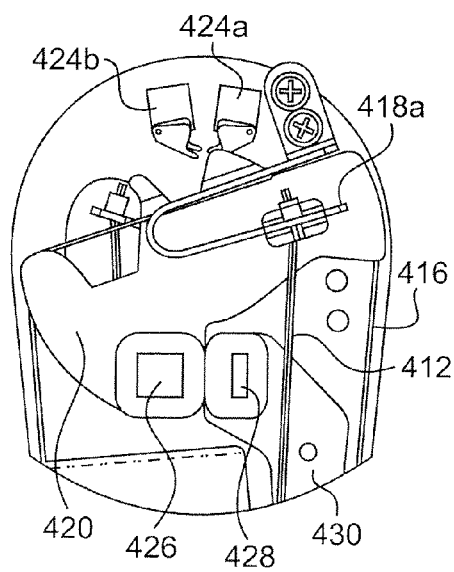
Figure 4E:
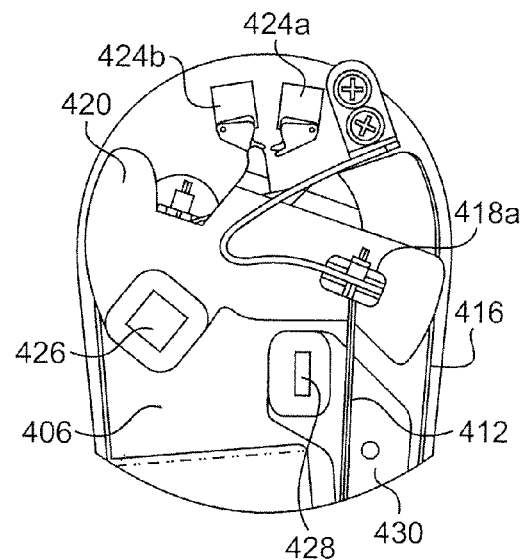
Figure 4F:
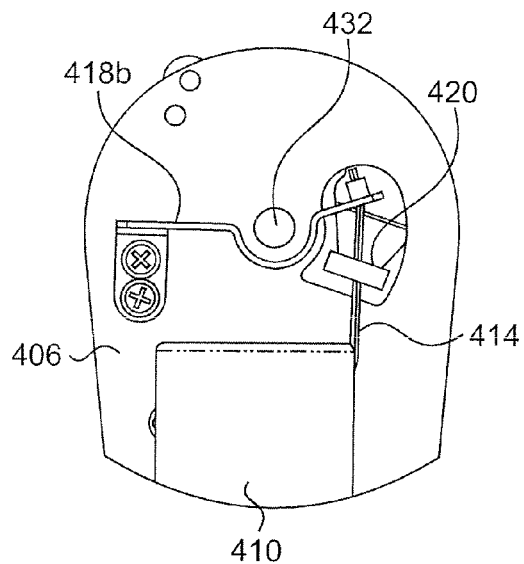
Figure 4G:
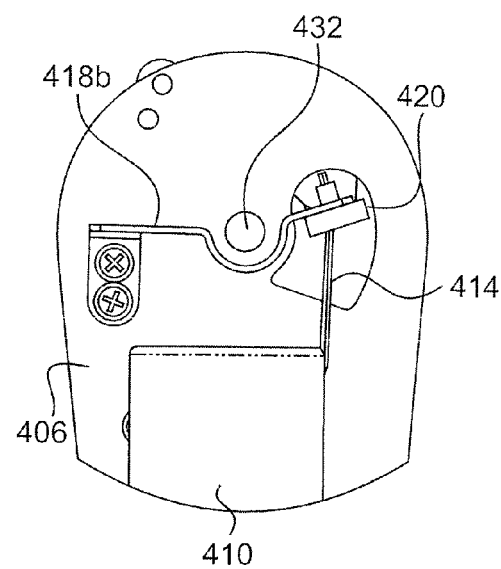

Additional details regarding the arrangement of the surgical tool 400 near the spring clip 418a, the spring clip 418b, and the rocking arm 420 are shown in FIGS. 4D through 4G. In particular, FIGS. 4D and 4E illustrate the operation of the surgical tool 400 on the side of the surgical tool 400 containing the wire 412 and the spring clip 418a. FIGS. 4F and 4G illustrate the operation of the surgical tool 400 on the side of the surgical tool 400 containing the wire 414 and the spring clip 418b.

As shown in FIGS. 4D and 4E, the spring clip 418a is attached or secured to the wire 412. The wire 412 can be contracted, such as by applying an electrical current to the wire 412. In FIG. 4D, the wire 412 has not been contracted, and the spring clip 418a is in its resting position. In FIG. 4E, the wire 412 has been contracted, which pulls down on the spring clip 418a. This imparts directional movement (clockwise in FIGS. 4D and 4E) to the rocking arm 420, which causes rotation in the wire 416, the pulley 422, and the surgical blade 408.

Two microswitches 424a-424b are used to control the rotation of the surgical blade 408. For example, prior to rotation of the surgical blade 408, the spring clip 418a or the rocking arm 420 may depress the microswitch 424a, which could inform the surgical tool 400 or an external component that the surgical tool 400 is ready for use (the blade is in an open position). During rotation of the surgical blade 408, the spring clip 418a or the rocking arm 420 stops depressing the microswitch 424a and eventually depresses the microswitch 424b. This could inform the surgical tool 400 or an external component that the surgical blade 408 has been rotated by a desired amount (such as an amount adequate to form a scleral tunnel in the patient's eye). The surgical tool 400 could then initiate counter-rotation of the surgical blade 408 to remove the surgical blade 408 from the patient's eye. This would cause the spring clip 418a or the rocking arm 420 to again depress the microswitch 424a. Each of the microswitches 424a-424b represents any suitable structure that can be contacted by an external element to trigger or interrupt a signal, such as any suitable switch that completes a circuit when depressed or that interrupts a circuit when depressed.

Two magnets 426-428 can be used as shown here to maintain the surgical blade 408 in an opened (unrotated) position. For example, the magnets 426-428 could be attracted to one another, and the magnets 426-428 could bias the rocking arm 420 in the position shown in FIG. 4D. The magnets 426-428 may maintain the rocking arm 420 in this position until the contraction of the wire 412 pulls the magnets 426-428 apart. As described below, contraction of the wire 414 may then allow the magnets 426-428 to move closer together, at which point the magnets 426-428 could again pull towards each other and bias the rocking arm 420 in the position shown in FIG. 4D. In this example, the magnet 426 is located within the rocking arm 420, and the magnet 428 is located within a magnet holder 430 that can be mounted on the printed circuit board 406 or other structure in the surgical tool 400. Also, the electrical current heating the wire 414 could stop prior to the complete removal of the surgical blade from the patient's eye, and the magnets 426-428 could complete the removal of the surgical blade.

As shown in FIGS. 4F and 4G, the spring clip 418b is attached or secured to the wire 414. In FIG. 4F, the wire 414 has not been contracted, and the spring clip 418b is in its resting position and is separated from a projection of the rocking arm 420. In FIG. 4G, the wire 412 has been contracted, which has caused movement of the rocking arm 420 around a pivot point 432. This therefore causes rotation of the surgical blade 408 into the patient's eye. At this point, the projection of the rocking arm 420 is now nearer to or in contact with one end of the spring clip 418b. The wire 414 can then be contracted, such as by applying an electrical current to the wire 414. This pulls down on the end of the spring clip 418b, which also pulls down on the projection of the rocking arm 420. This causes movement of the rocking arm 420 in the opposite direction and therefore rotation of the surgical blade 408 out of the patient's eye.

Figure 4H:
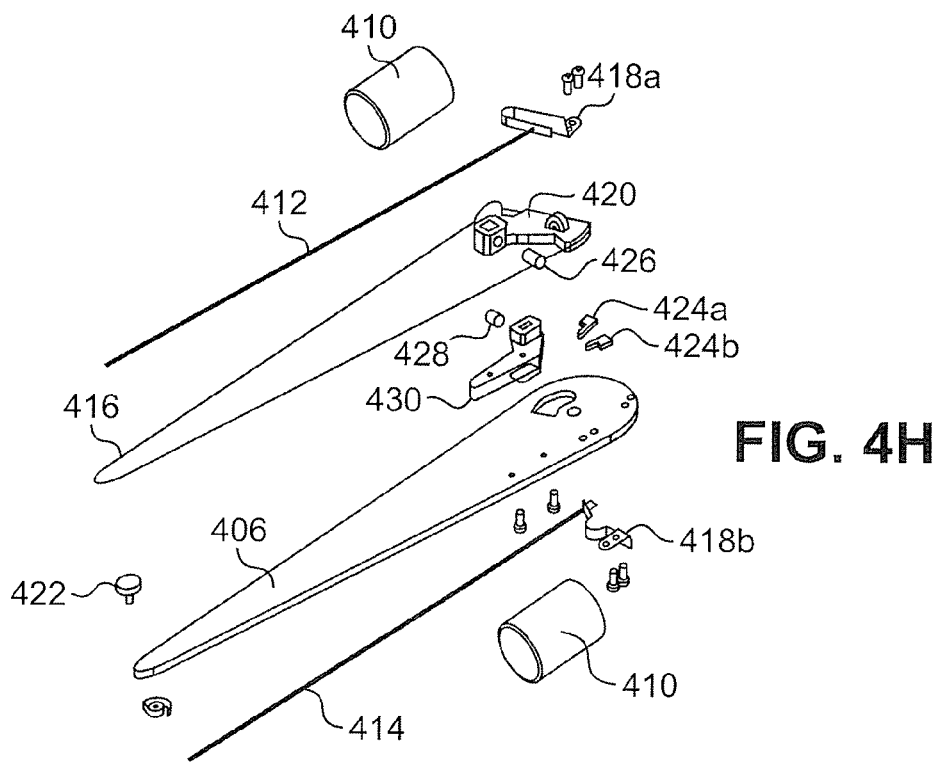
Figure 4I:
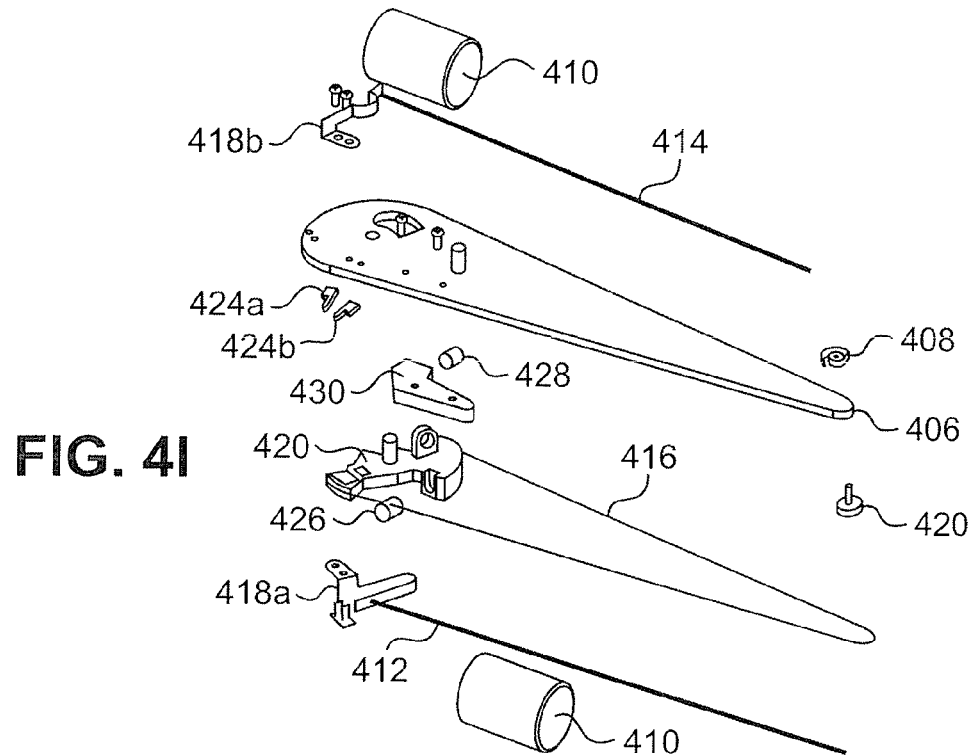

FIGS. 4H and 4I illustrate various additional details of the surgical tool 400. For example, these figures illustrate how various components in the surgical tool 400 are coupled together. These figures also illustrate the structures of various components in the surgical tool 400.

In particular embodiments, any of the surgical tools described above could include a removable portion, such as a removable module. The removable portion may contain various components that can be reused in multiple surgical tools. For instance, the components in a removable module could be reused in multiple surgical tools, while the other portions of each surgical tool could be disposable (such as after use of a tool for a single patient). This may, for example, eliminate the need to sterilize the disposable portions of the surgical tool between uses on different patients. In particular embodiments, the removable module of a surgical tool may include a power supply for the surgical tool, such as one or more batteries. The removable module could also include a printed circuit board containing the logic for controlling the surgical tool and wireless transmitter/receiver components. Any other or additional components could be contained within the removable portion of a surgical tool.

While microswitches 424a-424b are shown here as being used to monitor the movement of the rocking arm 420, other mechanisms could also be used. For example, the microswitches could be replaced with an optical encoder. An example optical encoder could include a semicircular or other structure with scale markings and an optical reader for reading the scale markings. The optical encoder could monitor the position of the rocking arm 420 by reading the scale markings on the structure as the rocking arm moves. This may allow the optical encoder to continuously monitor the position of the rocking arm 420 and thereby the position of the surgical blade. The optical encoder could also provide commands or data to other components of the surgical tool 400, such as upon completion or interruption of the rocking arm's rotation.

Figure 5A:
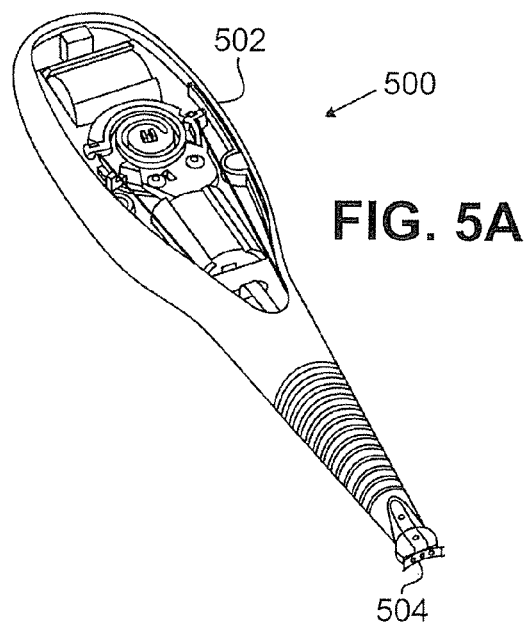
FIGS. 5A through 5Q illustrate a fifth example surgical tool for making incisions in accordance with this disclosure.
Figure 5B:
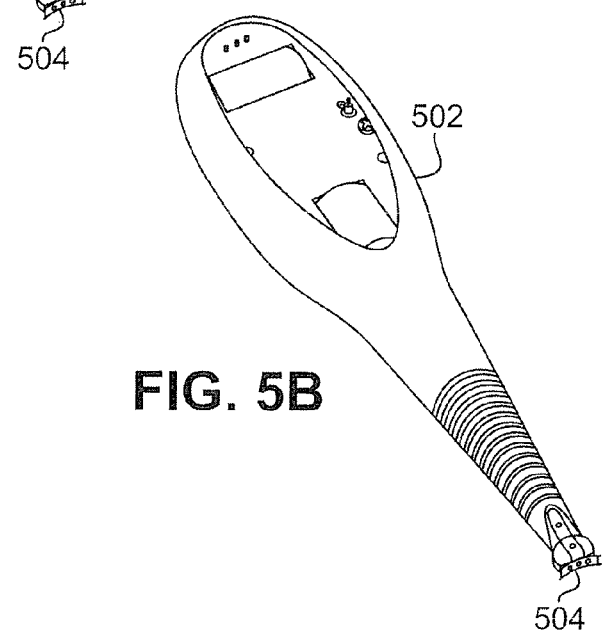
Figure 5C:
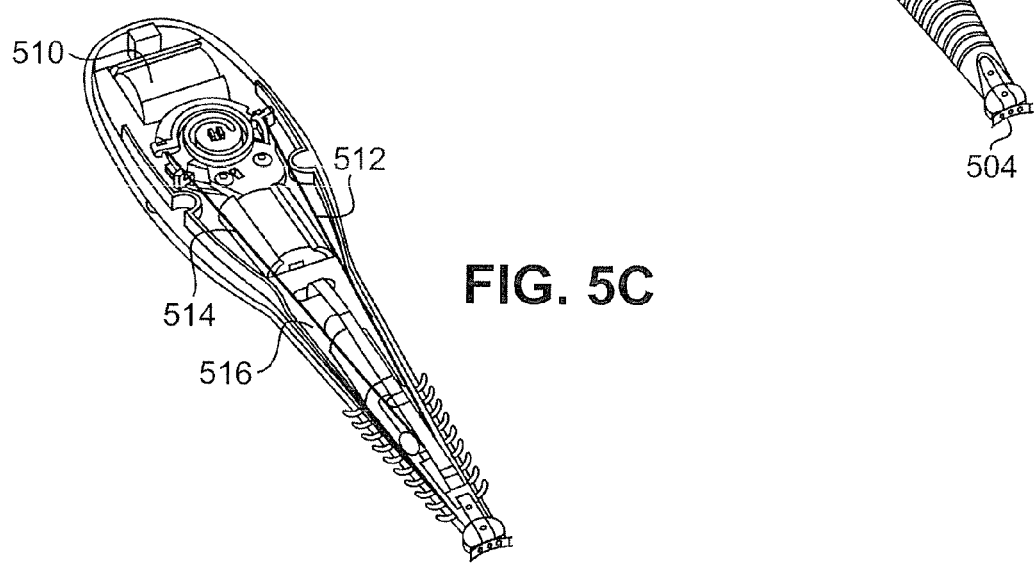
Figure 5D:
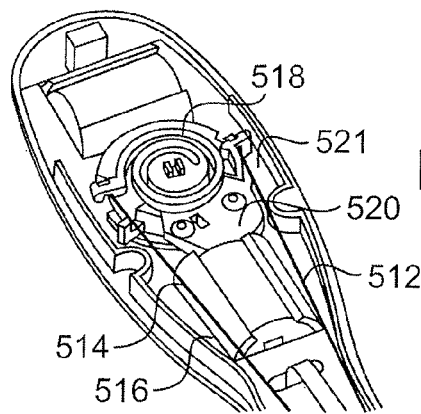
Figure 5E:
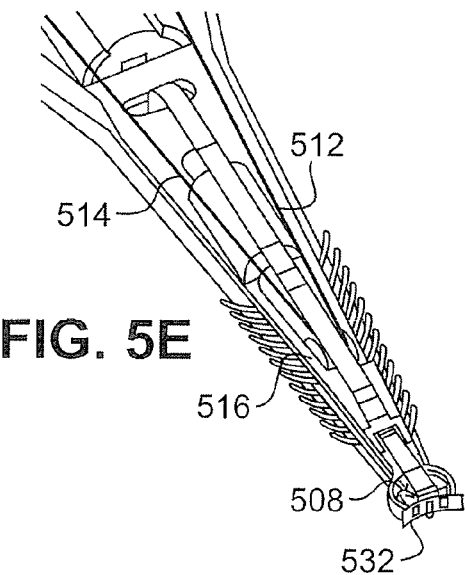
Figure 5F:
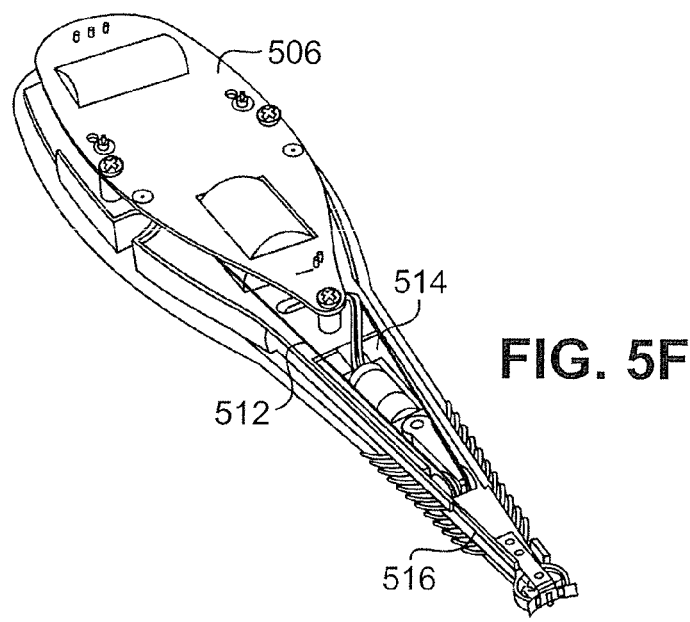
Figure 5G:
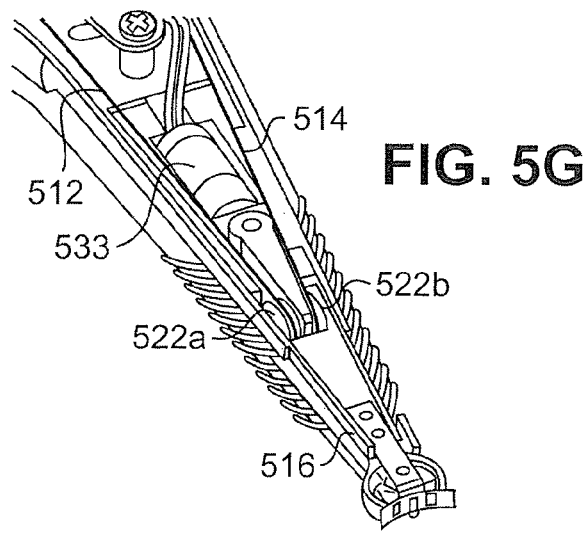
Figure 5H:
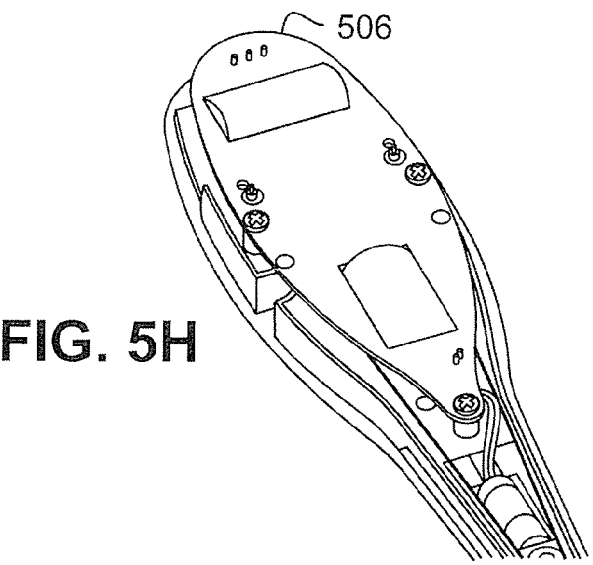
Figure 5I:
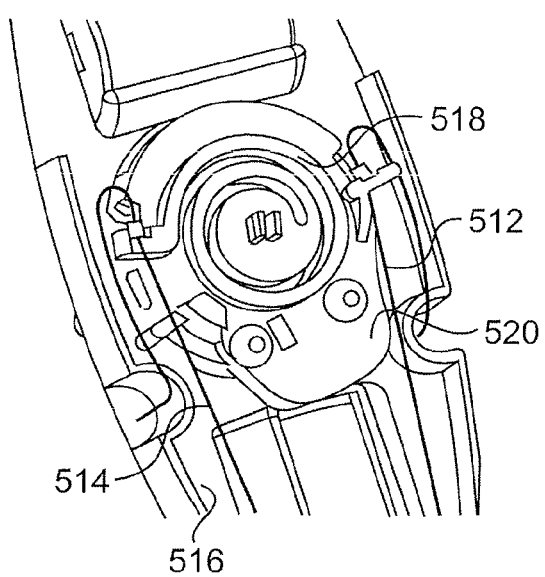
Figure 5J:
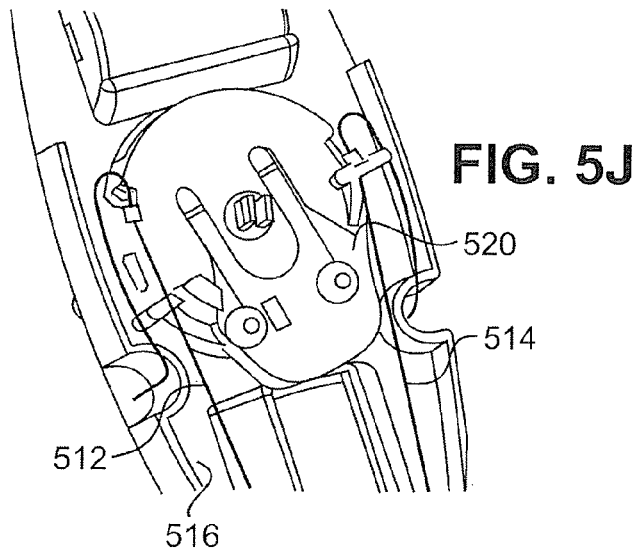
Figure 5K:
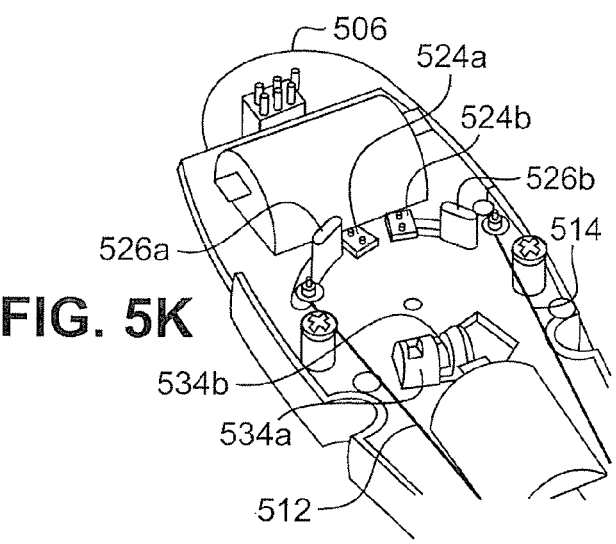
Figure 5L:
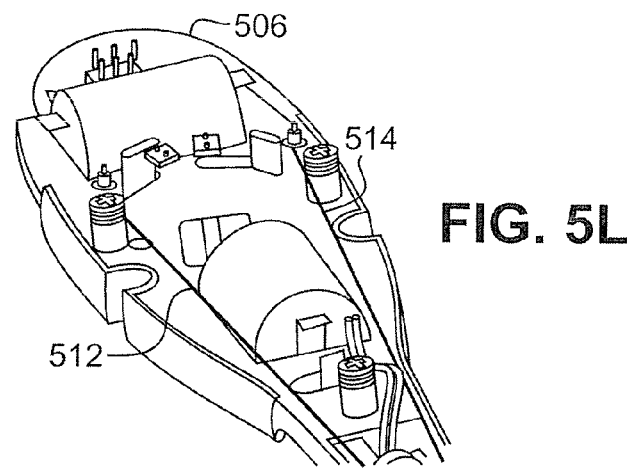
Figure 5M:
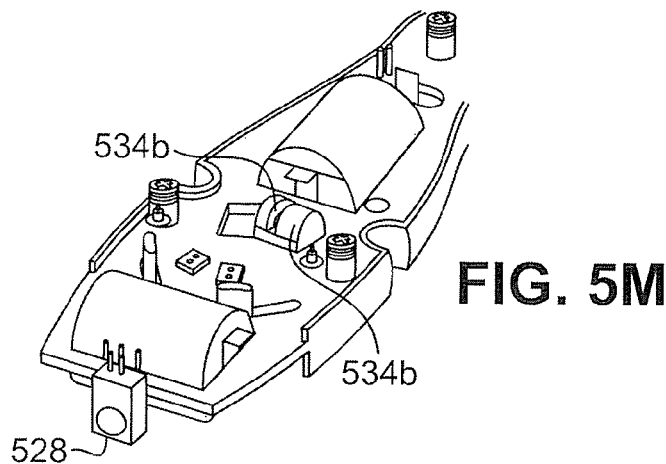
Figure 5N:
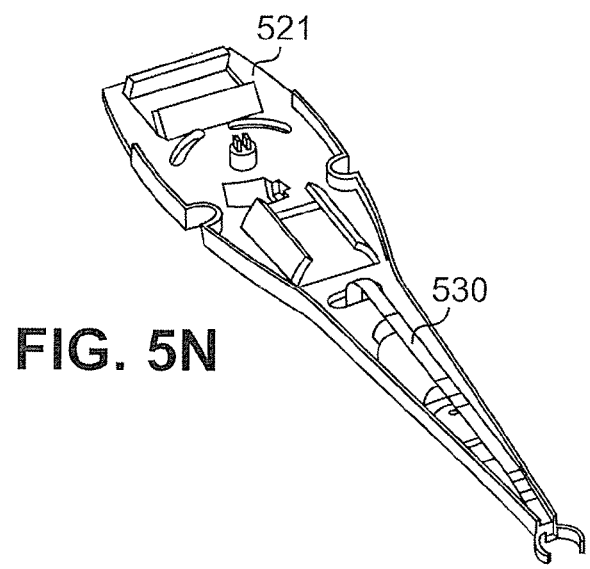
Figure 5O:
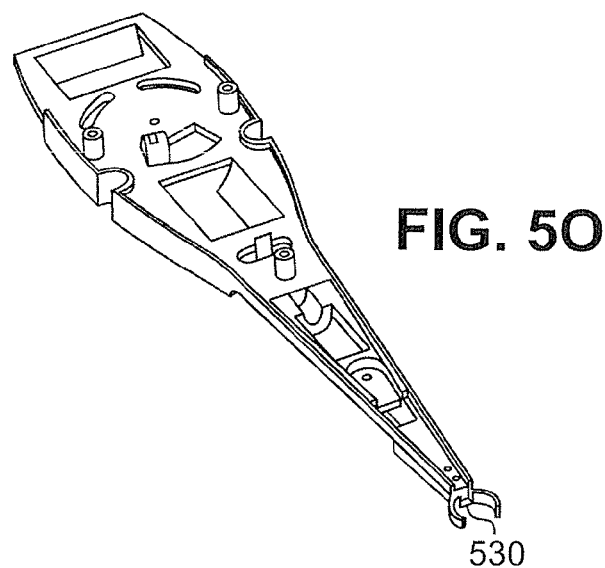
Figure 5P:
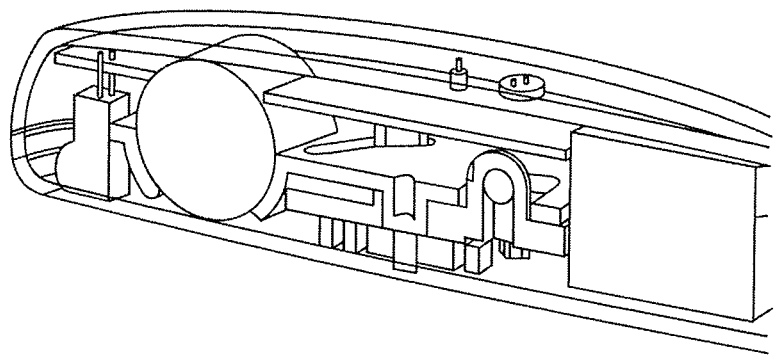
Figure 5Q:
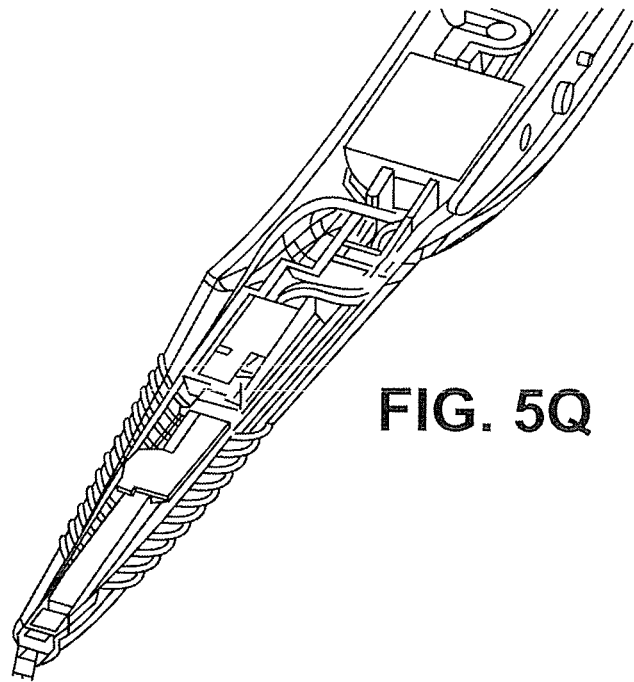

FIGS. 5A through 5Q illustrate a fifth example surgical tool 500 for making incisions in accordance with this disclosure. The embodiment of the surgical tool 500 shown in FIGS. 5A through 5Q is for illustration only. Other embodiments of the surgical tool 500 could be used without departing from the scope of this disclosure.

In this example, the surgical tool 500 may contain many of the same or similar components as described above. For example, the surgical tool 500 includes a housing 502 and a blade assembly 504. A printed circuit board 506 could support various functions performed by the surgical tool 500, such as by enabling and controlling rotation of a surgical blade 508. Also, one or more power supplies 510, such as one or more batteries, can supply power to the surgical tool 500.

Bi-directional rotation of the surgical blade 508 is created using three wires 512-516. One wire 512 extends generally from a rocking arm 520 (as shown in FIGS. 5D and 5I), around a pulley 522a, to the printed circuit board 506 (as shown in FIGS. 5K and 5L). Another wire 514 extends generally from a spring clip 518 (as shown in FIGS. 5D and 5I), around a pulley 522b, to the printed circuit board 506 (as shown in FIGS. 5K and 5L). The spring clip 518 and the rocking arm 520 are pivotally mounted on a frame 521. Each of the wires 512-514 could be formed from any suitable material(s), such as flexinol or other material(s) that can contract. The third wire 516 is connected at both ends to the rocking arm 520 and forms a loop around the surgical blade 508. The wire 516 could be formed from any suitable material(s), such as Kevlar. Each of the wires 512-516 could also have any suitable shape, such as a strand of material(s) having a circular or ovoidal cross section (although other shapes having over cross sections could be used).

In this example embodiment, contraction of the wires 512-514 may cause movement of the rocking arm 520, which may then impart bi-directional rotation to the wire 516 and therefore bi-directional rotation to the surgical blade 508. For example, as shown in FIG. 5I, contraction of the wire 512 may cause clockwise rotation of the rocking arm 520, which may rotate the surgical blade 508 in one direction. Contraction of the wire 514 may pull on the spring clip 518, which then pushes against the rocking arm 520 to cause counter-clockwise rotation of the rocking arm 520 and rotation of the surgical blade 508 in another direction. This counter-clockwise rotation of the rocking arm 520 may stretch the first wire 512 to regain a longer length and approximate its precharged condition. When an electrical current or other cause of the contraction of the second wire 514 stops, the spring clip 518 can then pull on the wire 514 to stretch the wire 514 so it may regain a longer length and approximate its precharged condition.

Two microswitches 524a-524b are used to control the rotation of the surgical blade 508. The microswitches 524a-524b could, for example, reside on the printed circuit board 506 or in any other suitable location(s). Two projections 526a-526b on the rocking arm 520 may move back and forth as the rocking arm 520 moves, and each projection 526a-526b may eventually depress one of the microswitches 524a-524b. In this way, the surgical tool 500 or an external component can determine when the surgical blade 508 has been rotated appropriately. Once again, it may be noted that while microswitches 524a-524b are shown here as being used to monitor the movement of the rocking arm 520, other mechanisms could also be used, such as an optical encoder.

The surgical tool 500 may include additional components for performing various functions. For example, as shown in FIG. 5M, a wireless transceiver 528 could be provided to enable wireless communications to and/or from the surgical tool 500. The wireless transceiver 528 could, for example, perform RF or infrared communications. The communications could be uni-directional (transmit only/receive only) or bi-directional.

As another example, as shown in FIGS. 5N and 5O, a ribbon cable 530 could be used in conjunction with the surgical blade 508. For instance, the surgical blade 508 could have a pliable footplate 532, which could become more flat as the footplate 532 is depressed against a patient's eye. When a certain level of depression is detected (such as when the footplate 532 is generally flat), the ribbon cable 530 could carry a signal to the printed circuit board 506, which could then trigger an audible, visual, and/or sensory (vibration) indicator 533 or other type of signal (either in the tool 500 or in an external component). In this way, the surgical tool 500 can inform a surgeon or other personnel when the surgical tool 500 has been properly placed on a patient's eye. The ribbon cable 530 could also be used to detect the position of the surgical blade in its movement/rotation (such as to detect if the blade has been rotated fully or gotten stuck during its rotation). As a further example, magnets 534a-534b could be attached to the frame 521 and the rocking arm 520, respectively. The magnets 534a-534b could be pulled apart during contraction of the wire 512. During contraction of the wire 514, after current stops flowing through the wire 514, the magnets 534a-534b could pull towards and contact each other, helping to facilitate removal of the surgical blade from the patient's eye. Any other or additional features could also be used in the surgical tool 500.

FIGS. 6A through 6E illustrate a sixth example surgical tool 600 for making incisions in accordance with this disclosure. The embodiment of the surgical tool 600 shown in FIGS. 6A through 6E is for illustration only. Other embodiments of the surgical tool 600 could be used without departing from the scope of this disclosure.

In this example, the surgical tool 600 may contain many of the same or similar components as described above. For example, the surgical tool 600 includes a housing 602 and a blade assembly 604. A printed circuit board 606 could support various functions performed by the surgical tool 600, such as by enabling and controlling rotation of a surgical blade in the blade assembly 604. Also, one or more power supplies 608, such as one or more batteries, can supply power to the surgical tool 600.

Bi-directional rotation of the surgical blade in the blade assembly 604 is created using three wires 610-614. One wire 610 extends generally from a spring clip 616, around a pulley 618, and up to the printed circuit board 606. Another wire 612 extends generally from a rocking arm 620, around a pulley 622, to the printed circuit board 606. The spring clip 616 and the rocking arm 620 are pivotally mounted on a frame. Each of the wires 610-612 could be formed from any suitable material(s), such as flexinol or other material(s) that can contract. The third wire 614 is connected at both ends to the rocking arm 620 and forms a loop around the surgical blade in the blade assembly 604. Two additional pulleys 624-626 are used here to guide the path of the wire 614. The wire 614 could be formed from any suitable material(s), such as Kevlar. Each of the wires 610-614 could also have any suitable shape, such as a strand of material(s) having a circular or ovoidal cross section (although other shapes having over cross sections could be used).

Figure 6A:
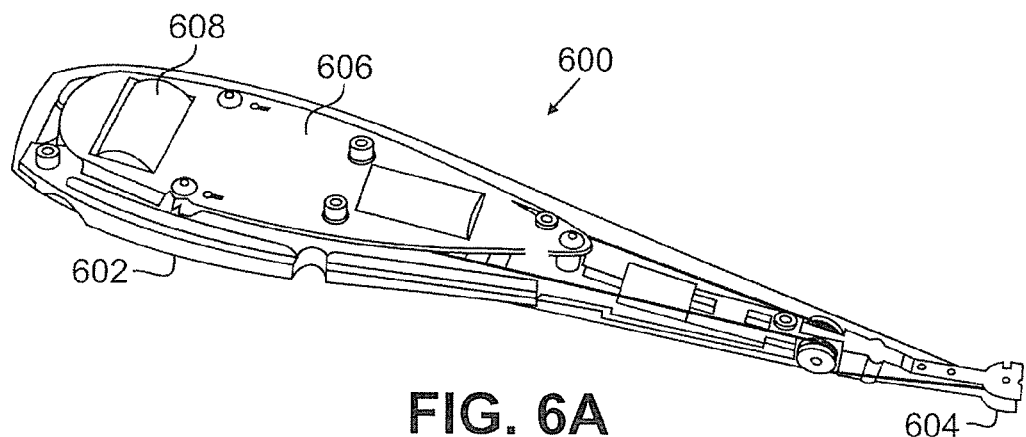
FIGS. 6A through 6E illustrate a sixth example surgical tool for making incisions in accordance with this disclosure.
Figure 6B:
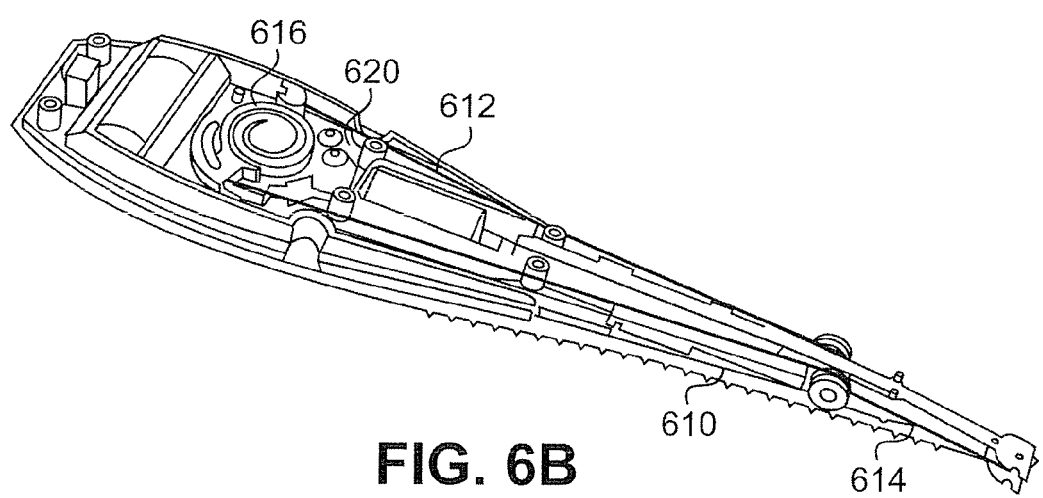
Figure 6C:
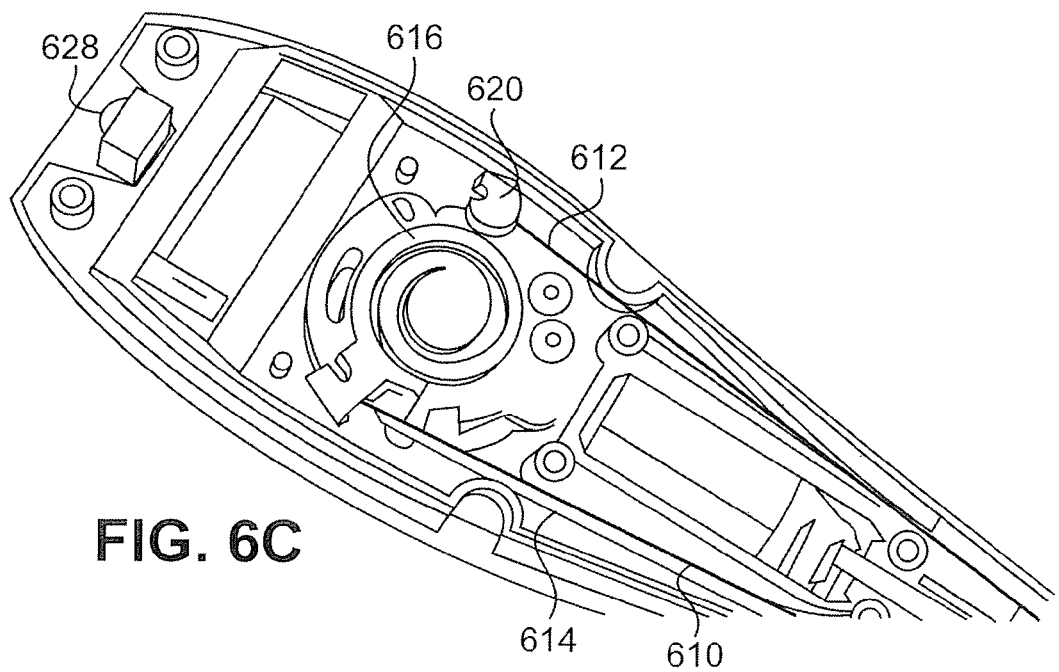
Figure 6D:
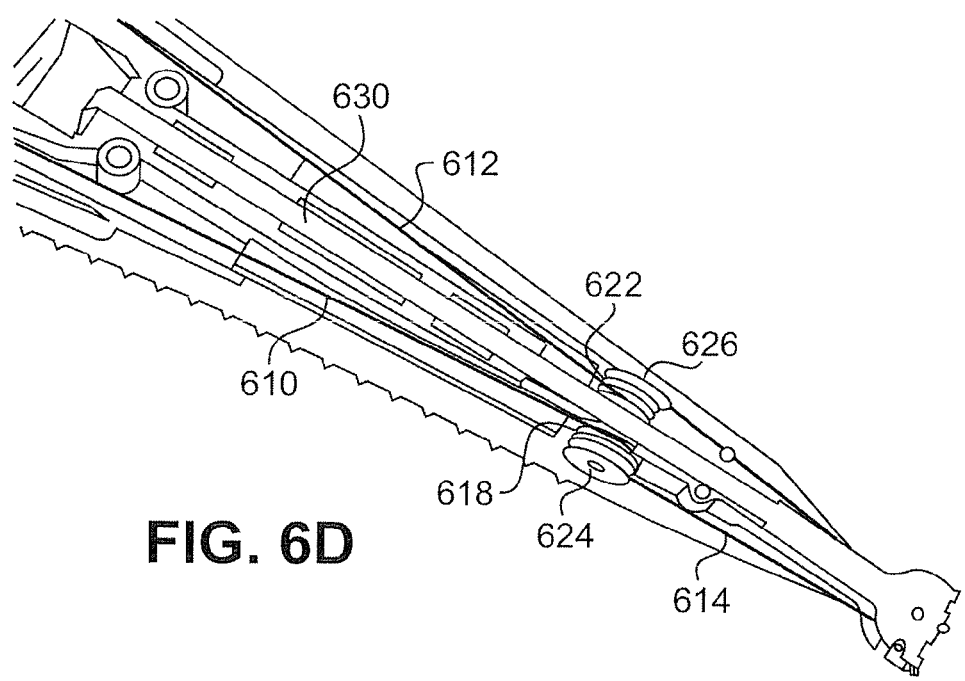
Figure 6E:
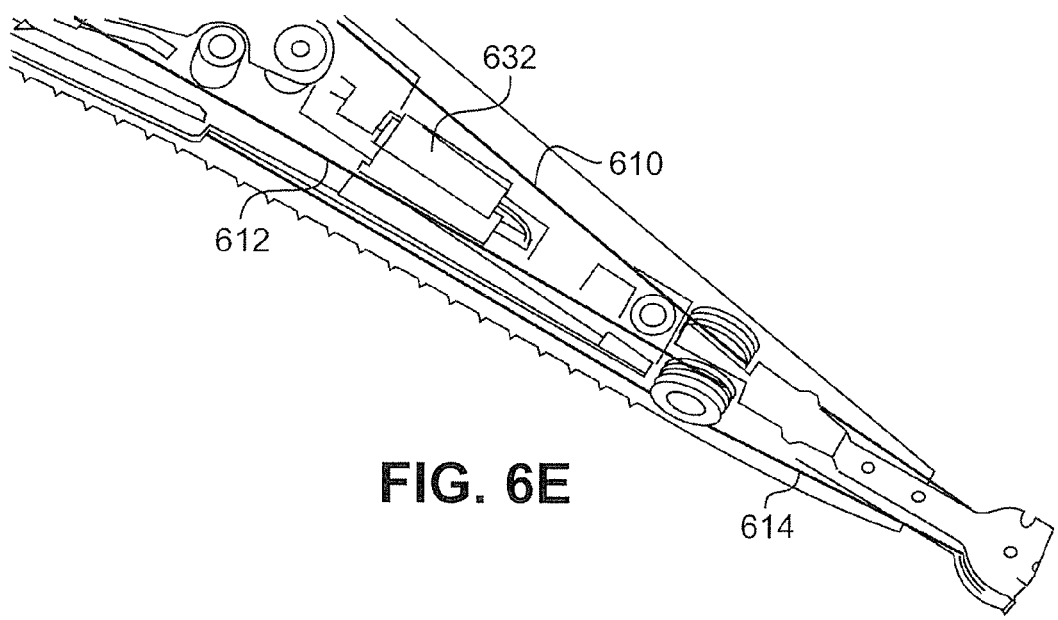

In this example embodiment, contraction of the wires 610-612 may cause movement of the rocking arm 620, which may then impart bi-directional rotation to the wire 614 and therefore bi-directional rotation to the surgical blade. For example, contraction of the wire 612 may cause clockwise rotation of the rocking arm 620 (as shown in FIG. 6B), which may rotate the surgical blade in one direction. Contraction of the wire 610 may pull on the spring clip 616, which then pushes against the rocking arm 620 to cause counter-clockwise rotation of the rocking arm 620 and rotation of the surgical blade in another direction. This counter-clockwise rotation of the rocking arm 620 may stretch the wire 612 to regain a longer length and approximate its precharged condition. When an electrical current or other cause of the contraction of the second wire 610 stops, the spring clip 616 can then pull on the wire 610 to stretch the wire 610 so it may regain a longer length and approximate its precharged condition.

The surgical tool 600 may include additional components for performing various functions. For example, a wireless transceiver 628 could be provided to enable wireless communications to and/or from the surgical tool 600, such as unidirectional or bi-directional RF or infrared communications. As another example, a ribbon cable 630 could be used in conjunction with the surgical blade, such as to detect when a pliable footplate is depressed against a patient's eye or to detect the position of the surgical blade in its rotation/movement. An audible, visual, and/or sensory indicator 632 could be used to produce notifications for an operator.

FIGS. 7A through 7H illustrate a seventh example surgical tool 700 for making incisions in accordance with this disclosure. The embodiment of the surgical tool 700 shown in FIGS. 7A through 7H is for illustration only. Other embodiments of the surgical tool 700 could be used without departing from the scope of this disclosure.

In this example embodiment, the surgical tool 700 includes a housing 702. The housing 702 holds or retains various components of the surgical tool 700. The housing 702 in this example includes a main body and a shaft. The housing 702 could have any suitable size and shape and be formed from any suitable material(s), such as plastic.

A surgical blade assembly 704 is coupled or secured to an end of the housing 702. The surgical blade assembly 704 includes a surgical blade 706, a footplate 708, and a blade housing 710. The surgical blade 706 includes projections that may fit through corresponding holes in the footplate 708 and/or the blade housing 710 to secure the surgical blade 706 in place. The footplate 708 helps to facilitate placement of the surgical tool 700 on the patient's eye and includes notches through which a cutting blade may pass.

A wire 712 is (among other things) wound around the surgical blade 706. Bi-directional rotation can be imparted to the wire 712 by other components in the surgical tool 700. The bi-directional rotation of the wire 712 causes a corresponding bi-directional rotation to the surgical blade 706, allowing the surgical blade 706 to be rotated into and then out of the ocular tissue of the patient's eye to form an incision. The wire 712 could be formed from any suitable material(s), such as Kevlar.

A switch assembly 714 can be used to control the surgical tool 700. For example, the switch assembly 714 can be used to initiate rotation of the wire 712 to rotate the surgical blade 706 into and out of the patient's ocular tissue. The switch assembly 714 includes an external portion that is accessible by a user outside of the housing 702, as well as an internal portion connecting the external portion to other internal components of the surgical tool 700.

In this example, a central cylinder 716 is located in the main body of the housing 702. As shown here, the wire 712 is wound around a central portion 717 of the cylinder 716 multiple times. As a result, the cylinder 716 can be used to impart bi-directional rotation to the wire 712, thereby helping to impart bi-directional rotation to the surgical blade 706.

Figure 7A:
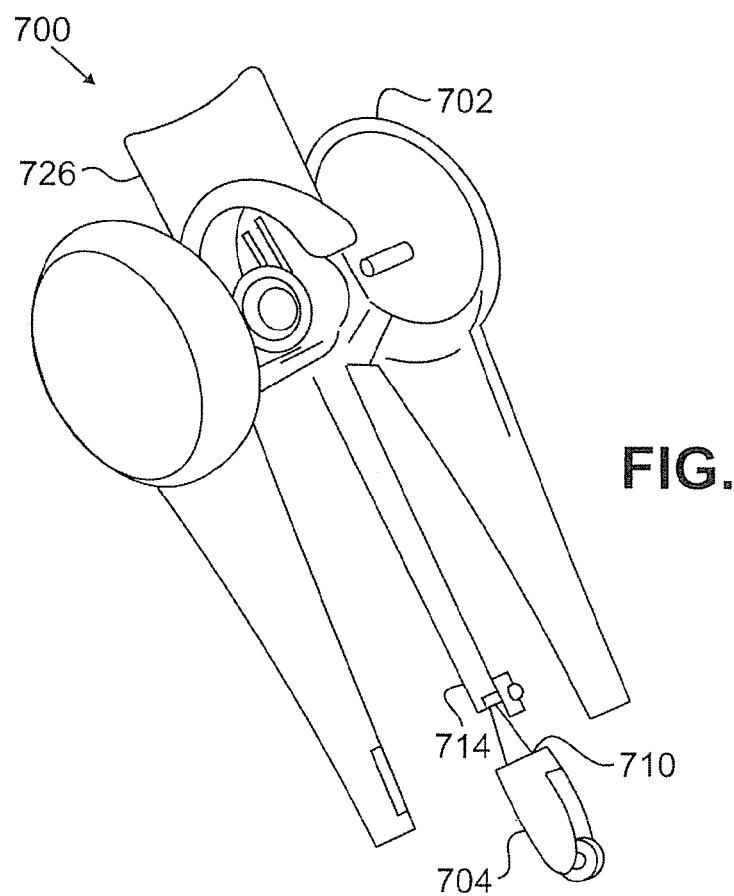
FIGS. 7A through 7H illustrate a seventh example surgical tool for making incisions in accordance with this disclosure.
Figure 7B:
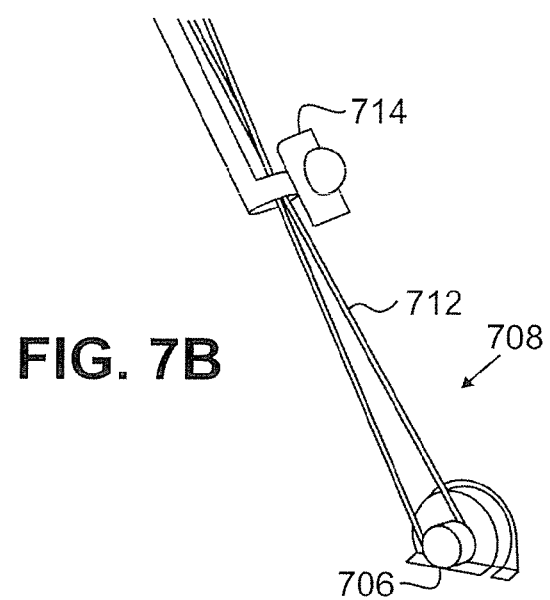
Figure 7C:
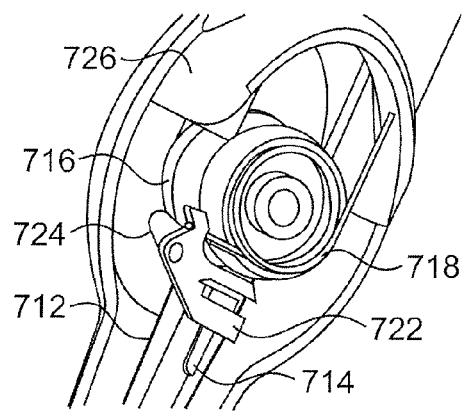
Figure 7D:
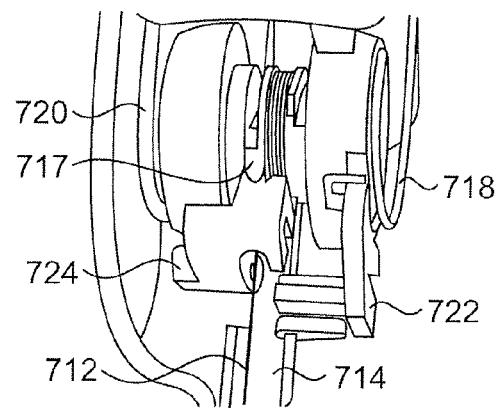

As shown in FIGS. 7C through 7F, two springs 718-720 and two latches 722-724 are used to control the rotation of the central cylinder 716. Here, one end of the spring 718 is inserted through a notch in the cylinder 716 and can be secured by the latch 722. Similarly, one end of the spring 720 is inserted through another notch in the cylinder 716 and can be secured by the latch 724 (as shown more clearly in FIGS. 7G and 7H). When the springs 718-720 are secured by the latches 722-724 (as shown in FIGS. 7C and 7D), the surgical blade 706 could be in its starting position.

Figure 7E:
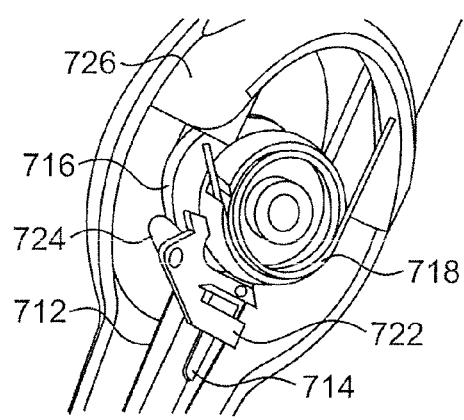
Figure 7F:
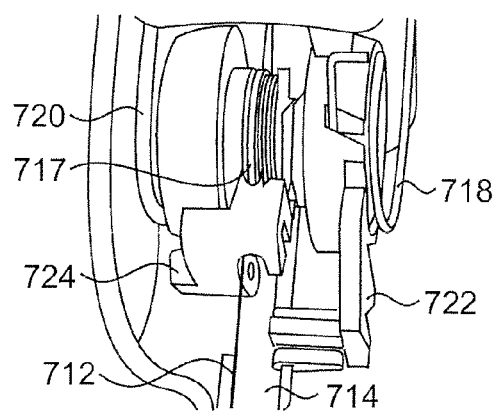

A user may then move the switch assembly 714 downward. The switch assembly 714 has a projection inserted through a slot of the latch 722. The latch 722 is rotatable, and the switch assembly 714 may pull down on one portion of the latch 722. This causes the portion of the latch 722 holding the spring 718 to pivot upward, releasing the spring 718. The spring 718 in this example is biased and pulls upward on the notch in the cylinder 716, causing the cylinder 716 to rotate clockwise (as seen in FIGS. 7C and 7E) or backwards (as seen in FIGS. 7D and 7F) while also pushing the central portion 717 closer to the spring 720 (as seen in FIGS. 7D and 7F). This imparts directional rotation to the surgical blade 706, causing the surgical blade 706 to rotate into the ocular tissue of the patient's eye.

A similar mechanism could be used with the spring 720 and the latch 724 to rotate the surgical blade 706 out of the ocular tissue of the patient's eye. The latch 724 could secure the spring 720 until the latch 724 is released, which could be triggered in any suitable manner (such as the movement of the central portion 717). The spring 720 may be stronger than the spring 718, meaning the spring 720 can provide greater rotational force than the spring 718. As a result, even with the spring 718 unsecured by its latch 722, the spring 720 can impart an opposite rotational force to the cylinder 716, causing the cylinder 716 to rotate counter-clockwise (as seen in FIGS. 7C and 7E) or forwards (as seen in FIGS. 7D and 7F). This causes the surgical blade 706 to rotate out of the ocular tissue of the patient's eye. Eventually, the end of the spring 718 returns to a position where it can be captured and secured by the latch 722. At that point, the user can move the switch assembly 714 up, rotating the latch 722 back into the position where the spring 718 is captured (thus going from the position shown in FIGS. 7E and 7F to the position shown in FIGS. 7C and 7D).

Figure 7G:
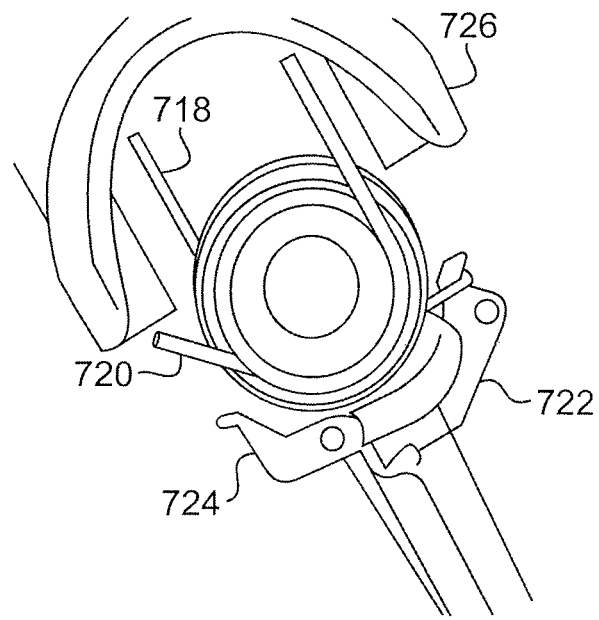
Figure 7H:
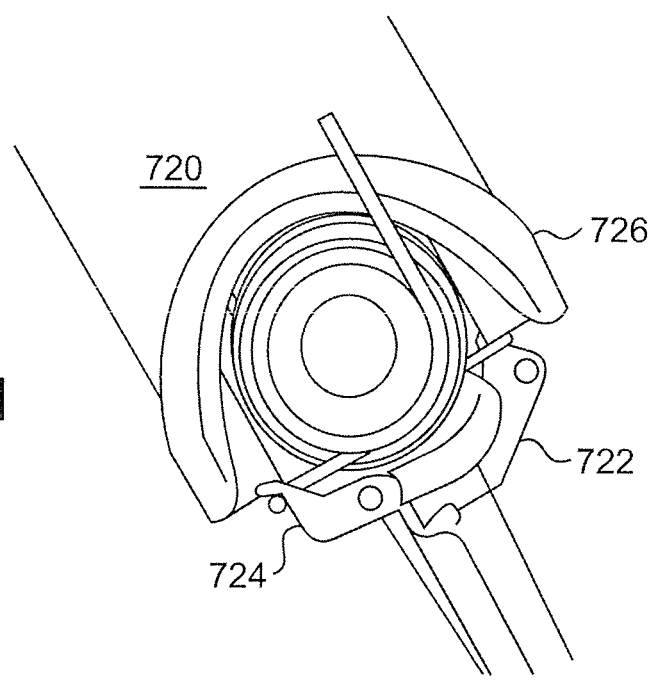
Figure 8A:
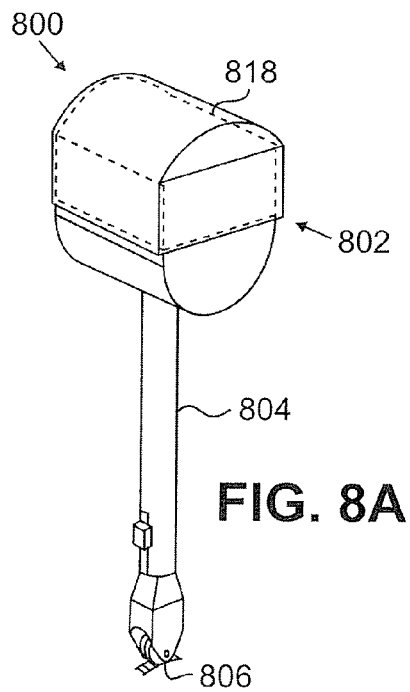
FIGS. 8A through 8D illustrate an eighth example surgical tool for making incisions in accordance with this disclosure.
Figure 8B:
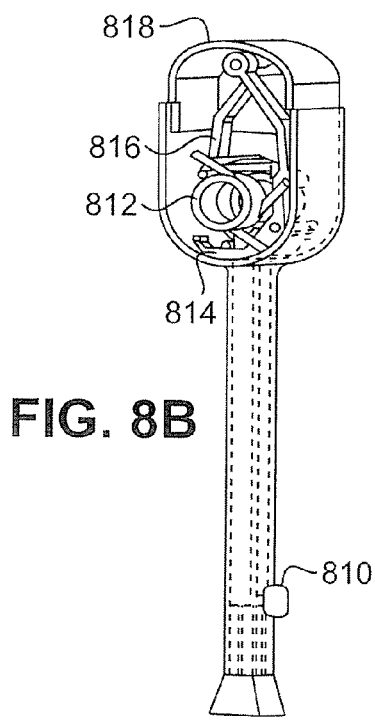
Figure 8C:
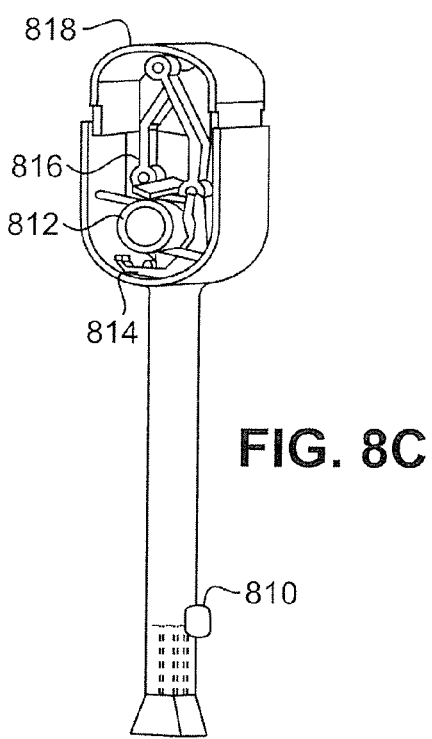
Figure 8D:
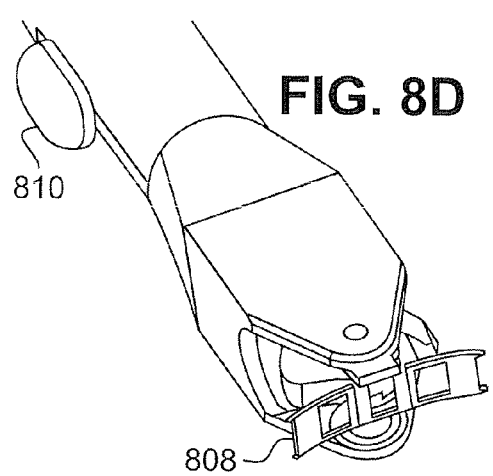
Figure 9A:
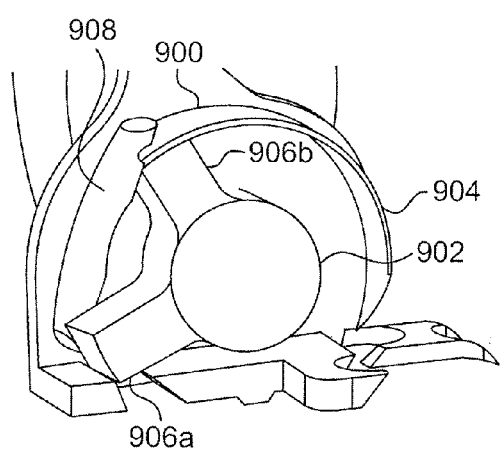
FIGS. 9A through 9D illustrate an example surgical blade assembly with an eye prosthesis for use with a surgical tool for making incisions in accordance with this disclosure.
Figure 9B:
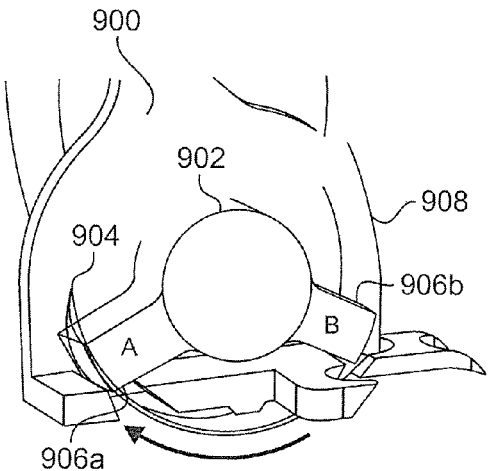
Figure 9C:
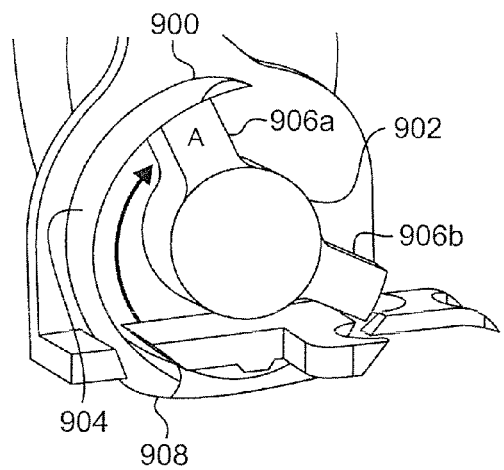
Figure 9D:
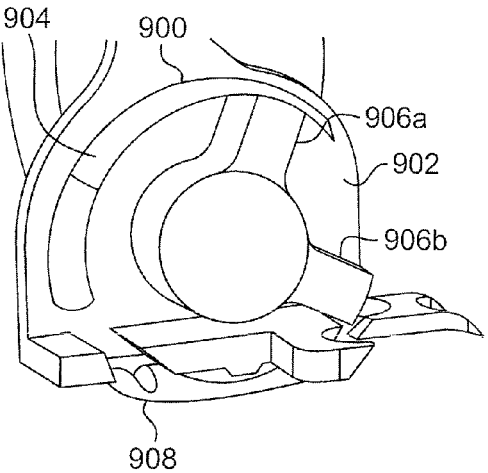

A return plunger 726 is used as shown in FIGS. 7G and 7H to return the spring 720 to its secured position. As shown here, the spring 720 can be moved by depressing the return plunger 726, which pushes the spring 720 down in FIGS. 7G and 7H until the spring 720 is captured by the latch 724. At this point, the return plunger 726 can be released and returned to its starting position. The surgical tool 700 is ready for reuse, such as for forming another incision in the same patient's eye(s).

FIGS. 8A through 8D illustrate an eighth example surgical tool 800 for making incisions in accordance with this disclosure. The embodiment of the surgical tool 800 shown in FIGS. 8A through 8D is for illustration only. Other embodiments of the surgical tool 800 could be used without departing from the scope of this disclosure.

In this example, the surgical tool 800 includes a body 802, a shaft 804, and a surgical blade assembly 806. The surgical blade assembly 806 includes a footplate 808, which in this embodiment is similar to the footplate 214 in FIGS. 2A through 2C. The footplate 808 includes notches through which a surgical blade can pass and prongs for securing the footplate 808 to the patient's eye. The footplate 808 may also rock back and forth on the surgical tool 800. However, in this example embodiment, the footplate 808 has a more rounded or arched shape. The footplate 808 could have any other suitable size, shape, or configuration.

The surgical tool 800 also includes a switch assembly 810 used to control the surgical tool 800. The surgical tool 800 further includes two springs 812, two latches 814, two mechanical arms 816, and a return plunger 818. The switch assembly 810, springs 812, and latches 814 could operate in the same or similar manner as the surgical tool 700 in FIGS. 7A through 7H. For example, one latch 814 could release one spring 812 in response to downward movement of the switch assembly 810, allowing a surgical blade to be rotated in one direction. Another latch 814 could then release another spring 812, allowing the surgical blade to be rotated in the opposite direction. The mechanical arms 816 can be used to return the springs 812 to a desired position based on downward movement of the return plunger 818. Upward movement of the return plunger 818 allows the mechanical arms 816 to release the springs 812.

In particular embodiments, the surgical tool 700 shown in FIGS. 7A through 7H or the surgical tool 800 shown in FIGS. 8A through 8D could represent a disposable tool that is used on one patient and then discarded. While the surgical tool 700 or 800 is sterilized prior to its use on a patient, this may help to avoid the need to re-sterilize the tool 700 or 800.

Although FIGS. 1A through 8D illustrate various examples of surgical tools for making incisions, various changes could be made to these figures. For example, the arrangement and layout of the components in each surgical tool are for illustration only, and other arrangements and layouts of the components in each tool could be used. Also, various components in each tool could be combined or omitted and additional components could be added according to particular needs. Further, various components in each tool could be replaced by other components performing the same or similar functions. Moreover, various features shown or described with respect to one or more of the surgical tools could be used with others of the surgical tools. Beyond that, other or additional mechanisms could be used to cause rotation of a surgical blade in a surgical tool, such as an electric motor. The surgical blade could also be moved manually, such as by using a wheel controlled by a surgeon's thumb or other part of the surgeon's hand to manually rotate the surgical blade. In addition, some of these figures have illustrated various surgical tools in which a surgical blade is rotated or otherwise moved based on changing the length of one or more flexinol or other wires. The same or similar technique could be used in any other suitable surgical tool (whether or not that surgical tool is used to make incisions in a patient's eye).

FIGS. 9A through 9D illustrate an example surgical blade assembly 900 with an eye prosthesis for use with a surgical tool for making incisions in accordance with this disclosure. The embodiment of the surgical blade assembly 900 shown in FIGS. 9A through 9D is for illustration only. Other embodiments of the surgical blade assembly 900 could be used without departing from the scope of this disclosure.

In this example, the surgical blade assembly 900 is used to form an incision and to implant a scleral prosthesis or other implant. The surgical blade assembly 900 could be used with any of the surgical tools disclosed in this patent document.

As shown here, the surgical blade assembly 900 includes a central portion 902, a cutting blade 904, and hub arms 906a-906b. The central portion 902 can be rotated in multiple directions to move the cutting blade 904 into and out of the scleral tissue of a patient's eye. The hub arms 906a-906b couple the central portion 902 to the cutting blade 904, helping to translate rotation of the central portion 902 into movement of the cutting blade 904.

A scleral prosthesis 908 is engaged with the tail end of the cutting blade 904. As shown here, the cutting blade 904 is initially rotated through the scleral tissue of the patient's eye using the hub arm 906b. Eventually, the hub arm 906a engages with the tip of the cutting blade 904, and the hub arm 906b disengages from the cutting blade 904. The hub arm 906a then continues to rotate the cutting blade 904 through the scleral tissue and out of the newly formed scleral tunnel. In this example, the scleral prosthesis 908 is pulled into the scleral tunnel upside-down by the cutting blade 904 and then disengages from the cutting blade 904. The prosthesis 908 can then be rotated (such as by a surgeon or other personnel using a surgical instrument to manually rotate the prosthesis 908) to properly position the prosthesis 908 in the newly-formed scleral tunnel.

The technique shown in FIGS. 9A through 9D is for illustration only. Any other suitable technique could be used to implant a scleral prosthesis into a scleral tunnel. For example, the surgical blade assembly 900 could include a single hub arm, and the surgical blade assembly 900 could rotate the cutting blade 904 into scleral tissue and then out of the scleral tissue to form a scleral tunnel. The prosthesis 908 could then be inserted into the scleral tunnel using any other suitable tool or technique.

Although FIGS. 9A through 9D illustrate one example of a surgical blade assembly 900 with an eye prosthesis for use with a surgical tool for making incisions, various changes may be made to FIGS. 9A through 9D. For example, any other suitable technique could be used to form a scleral tunnel in a patient's eye. The formation of the scleral tunnel may or may not include the simultaneous or near-simultaneous implantation of a scleral prosthesis into the scleral tunnel.

Figure 10A:
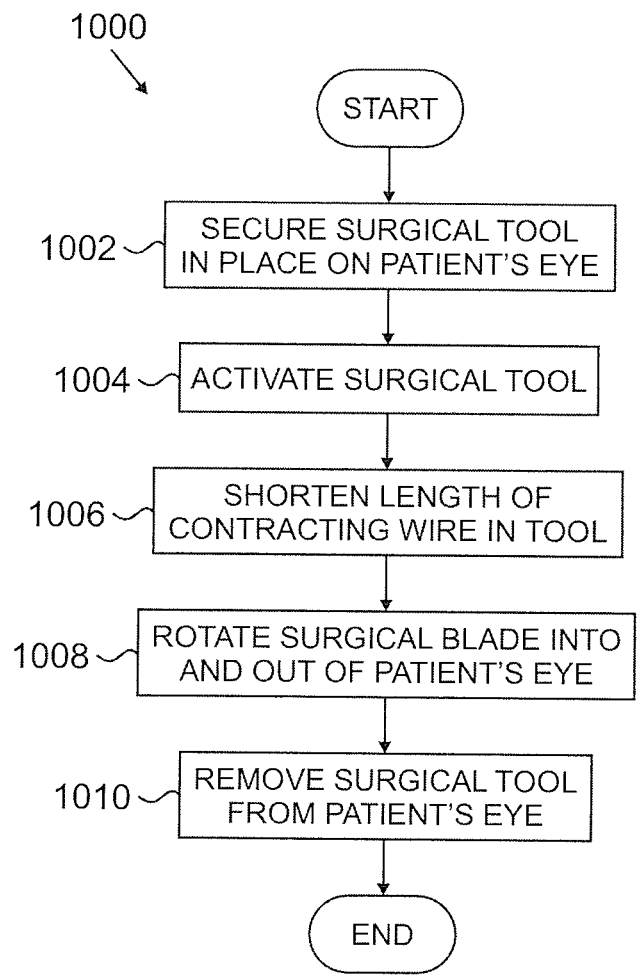
FIGS. 10A and 10B illustrate example methods for making incisions in accordance with this disclosure.
Figure 10B:
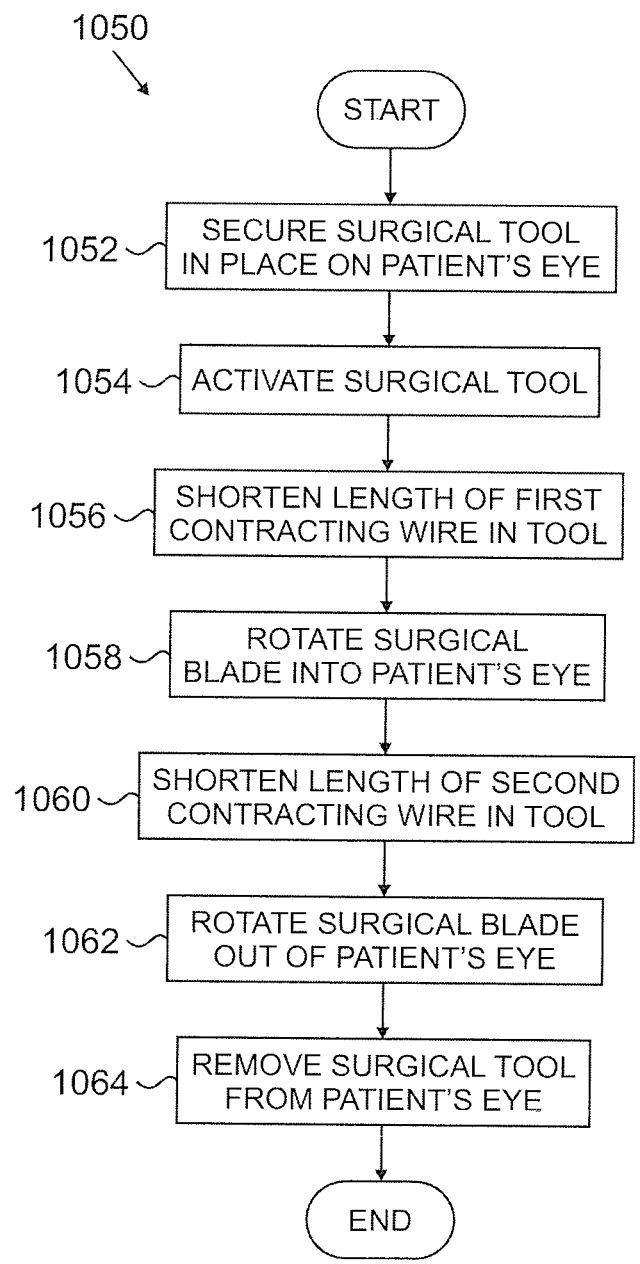

FIGS. 10A and 10B illustrate example methods 1000 and 1050 for making incisions in accordance with this disclosure. The embodiments of the methods 1000 and 1050 shown in FIGS. 10A and 10B are for illustration only. Other embodiments of the methods 1000 and 1050 could be used without departing from the scope of this disclosure.

In FIG. 10A, a surgical tool is secured to a patient's eye at step 1002. This could include, for example, placing the surgical tool on the patient's eye in the proper location and using the footplate of the surgical tool to maintain that position. This could also include mounting the surgical tool on an ocular fixation device that has been placed on the patient's eye.

The surgical tool is activated at step 1004. This could include, for example, moving a switch located on the surgical tool into the proper position. This could also include using a foot pedal or other external device or structure to send a wired or wireless command to the surgical tool.

The length of a contracting wire in the surgical tool is shortened at step 1006. This could include, for example, heating a wire formed from flexinol, such as by using an electrical current. The heat created in the flexinol wire by the electrical current causes the flexinol wire to shorten or contract, reducing its overall length in the surgical tool.

A surgical blade is rotated into and out of a patient's eye at step 1008. This could include, for example, the contracting wire causing a locomotive wheel 132 to turn, which causes a locomotive arm 134 to move a wire 114, which causes a rotating wheel 108 to rotate a surgical blade 106. The locomotive wheel 132 can be rotated at or near 360°, which means the locomotive arm 134 imparts bi-directional rotation to the wire 114. This also imparts bi-directional rotation to the surgical blade 106, allowing the surgical blade 106 to move into and then out of the patient's ocular tissue.

The surgical tool can be removed from the patient's eye at step 1010. This may include, for example, moving the surgical tool from one location to another to form another incision. This could also include removing the surgical tool so that additional surgical steps or procedures can occur, such as the implanting of a scleral prosthesis or other device in the incision.

In FIG. 10B, a surgical tool is secured to a patient's eye at step 1052, and the surgical tool is activated at step 1054. The length of a first contracting wire in the surgical tool is shortened at step 1056, such as by applying an electrical current to a first flexinol wire. A surgical blade is rotated into a patient's eye at step 1058. This could include, for example, the first contracting wire pulling on a surgical blade 212. The first contracting wire could, for instance, be wrapped around a surgical blade 212 and pull/rotate the surgical blade 212 in one direction.

The length of a second contracting wire in the surgical tool is shortened at step 1060, such as by applying an electrical current to a second flexinol wire. The surgical blade is rotated out of the patient's eye at step 1062. This could include, for example, the second contracting wire pulling on the surgical blade 212. The second contracting wire could, for instance, be wrapped around the surgical blade 212 and pull/rotate the surgical blade 212 in the opposite direction (compared to the direction of rotation caused by the first contracting wire). The surgical tool can be removed from the patient's eye at step 1064.

Although FIGS. 10A and 10B illustrate examples of methods 1000 and 1050 for making incisions, various changes may be made to FIGS. 10A and 10B. For example, while shown as a series of steps, various steps in FIGS. 10A and 10B could overlap, occur in parallel, occur in a different order, or occur multiple times. Also, other mechanisms could be used to translate contraction of one or more wires into single- or multi-directional rotation of a surgical blade. In addition, similar methods could be used to form incisions in other areas and need not be limited to use with just ocular incisions.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video/versatile disc (DVD), or any other type of memory.

It may be advantageous to set forth definitions of certain words and phrases used throughout this patent document. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A surgical tool comprising:
   a surgical blade configured to be rotated to form an incision;
   multiple wires configured to cause bidirectional rotation of the surgical blade; and
   an actuator configured to shorten lengths of at least some of the wires by applying electrical currents to at least some of the wires to cause the bidirectional rotation of the surgical blade;
   wherein:
   the wires comprise a first wire, a second wire, and a third wire; and
   the third wire is configured to rotate the surgical blade in a first direction in response to shortening the length of the first wire and to rotate the surgical blade in a second direction in response to shortening the length of the second wire.

2. The surgical tool of claim 1, wherein the surgical tool further comprises:
   a first connector coupling the first wire to the third wire such that the shortening of the length of the first wire rotates the surgical blade in the first direction; and
   a second connector coupling the second wire to the third wire such that the shortening of the length of the second wire rotates the surgical blade in the second direction.

3. The surgical tool of claim 1, wherein the surgical tool further comprises:
   a rocking arm coupled to the third wire and configured to rotate;
   a first spring clip coupled to the first wire and the rocking arm such that the shortening of the length of the first wire rotates the rocking arm clockwise; and
   a second spring clip coupled to the second wire and the rocking arm such that the shortening of the length of the second wire rotates the rocking arm counter-clockwise.

4. The surgical tool of claim 3, wherein the surgical tool further comprises:
   a first switch configured to indicate when the rocking arm has rotated to a first position in response to the shortening of the length of the first wire;
   a second switch configured to indicate when the rocking arm has rotated to a second position in response to the shortening of the length of the second wire; and
   at least one magnet configured to pull the rocking arm into the second position.

5. The surgical tool of claim 3, wherein the surgical tool further comprises:
   an optical encoder configured to continuously monitor a position of the rocking arm.

6. The surgical tool of claim 1, wherein the surgical tool further comprises:
   a rocking arm coupled to the first and third wires and configured to rotate such that the shortening of the length of the first wire rotates the rocking arm clockwise; and
   a spring clip coupled to the second wire and the rocking arm such that the shortening of the length of the second wire rotates the rocking arm counter-clockwise.

7. The surgical tool of claim 6, wherein:
   the rotation of the rocking arm in response to the shortening of the length of the second wire stretches the first wire; and
   the spring clip is configured to stretch the second wire after the rotation of the surgical blade in the second direction.

8. The surgical tool of claim 1, wherein the surgical tool further comprises:
a wireless transceiver configured to at least one of transmit data wirelessly and receive data wirelessly.

9. The surgical tool of claim 1, wherein the surgical tool further comprises:
a projection configured to couple the surgical tool to an ocular fixation device.

10. The surgical tool of claim 1, wherein the surgical blade comprises a curved cutting blade configured to be rotated into scleral tissue of a patient's eye.

11. The surgical tool of claim 1, wherein the at least some of the wires comprise flexible nitinol.

12. The surgical tool of claim 1, wherein the actuator comprises a printed circuit board configured to apply the electrical currents to the wires.

13. The surgical tool of claim 12, wherein the printed circuit board is further configured to trigger multiple audible, sensory, or visual notifications, the audible, sensory, or visual notifications including notifications that:
the surgical tool is properly located and ready for use;
the surgical blade is moving in the first direction;
the surgical blade is moving in the second direction;
a cycle of the surgical blade in the first and second directions has been interrupted; and
the cycle of the surgical blade in the first and second directions has been successfully completed.

14. The surgical tool of claim 12, wherein the printed circuit board is further configured to receive commands from an operator.

15. A method comprising:
shortening lengths of at least first and second wires in a surgical tool by applying electrical currents to the first and second wires; and
imparting bidirectional rotation to a surgical blade of the surgical tool based on the shortening of the lengths of the first and second wires;
wherein imparting the bidirectional rotation to the surgical blade comprises using a third wire to rotate the surgical blade in a first direction in response to shortening the length of the first wire and using the third wire to rotate the surgical blade in a second direction in response to shortening the length of the second wire.

16. The method of claim 15, wherein the first and second wires comprise flexible nitinol.

17. The method of claim 15, wherein:
the third wire is coupled to the first and second wires; and
the shortening of each of the first and second wires pulls on the third wire.

18. The method of claim 15, wherein:
the third wire is coupled to a rocking arm;
the shortening of the length of the first wire rotates the rocking arm and moves the third wire in one direction; and
the shortening of the length of the second wire rotates the rocking arm and moves the third wire in an opposite direction.

19. The method of claim 18, wherein:
at least one of the first and second wires is coupled to at least one spring clip attached to the rocking arm; and
further comprising pulling on at least one of the first and second wires using the at least one spring clip to lengthen at least one of the first and second wires.

20. The method of claim 15, wherein:
the first and third wires are coupled to a rocking arm;
the shortening of the length of the first wire pulls on the rocking arm and rotates the rocking arm in one direction; and
the shortening of the length of the second wire pulls on a spring clip coupled to the rocking arm and rotates the rocking arm in an opposite direction.

21. The method of claim 20, wherein:
the rotation of the rocking arm in response to the shortening of the length of the second wire stretches the first wire; and
the spring clip stretches the second wire after the rotation of the rocking arm in the second direction.

22. A system comprising:
an ocular fixation device configured to be secured to ocular tissue of an eye; and
a surgical tool configured to be mounted on the ocular fixation device, the surgical tool comprising:
a surgical blade configured to be rotated to form an incision in the ocular tissue;
multiple wires configured to cause bidirectional rotation of the surgical blade; and
an actuator configured to shorten lengths of at least some of the wires applying electrical currents to at least some of the wires to cause the bidirectional rotation of the surgical blade;
wherein:
the wires comprise a first wire, a second wire, and a third wire; and
the third wire is configured to rotate the surgical blade in a first direction in response to shortening the length of the first wire and to rotate the surgical blade in a second direction in response to shortening the length of the second wire.

23. The system of claim 22, wherein the surgical tool further comprises:
a first connector coupling the first wire to the third wire such that the shortening of the length of the first wire rotates the surgical blade in the first direction; and
a second connector coupling the second wire to the third wire such that the shortening of the length of the second wire rotates the surgical blade in the second direction.

24. The system of claim 22, wherein the surgical tool further comprises:
a rocking arm coupled to the third wire and configured to rotate;
a first spring clip coupled to the first wire and the rocking arm such that the shortening of the length of the first wire rotates the rocking arm clockwise; and
a second spring clip coupled to the second wire and the rocking arm such that the shortening of the length of the second wire rotates the rocking arm counter-clockwise.

25. The system of claim 22, wherein the surgical tool further comprises:
a rocking arm coupled to the first and third wires and configured to rotate such that the shortening of the length of the first wire rotates the rocking arm clockwise; and
a spring clip coupled to the second wire and the rocking arm such that the shortening of the length of the second wire rotates the rocking arm counter-clockwise.

* * * * *